(12) United States Patent
Athma et al.

(10) Patent No.: US 7,499,805 B2
(45) Date of Patent: *Mar. 3, 2009

(54) METHOD AND APPARATUS FOR PROTEIN STRUCTURE ANALYSIS

(75) Inventors: Prasanna Athma, Yorktown Heights, NY (US); Ajay K. Royyuru, Congers, NY (US); Benjamin David Silverman, Yorktown Heights, NY (US); Ruhong Zhou, Fort Lee, NJ (US)

(73) Assignee: International Business Machines Corporation, Armonk, NY (US)

( * ) Notice: Subject to any disclaimer, the term of this patent is extended or adjusted under 35 U.S.C. 154(b) by 1120 days.

This patent is subject to a terminal disclaimer.

(21) Appl. No.: 10/295,290

(22) Filed: Nov. 15, 2002

(65) Prior Publication Data

US 2004/0096897 A1 May 20, 2004

(51) Int. Cl.
*G06F 17/11* (2006.01)
*G06F 17/50* (2006.01)
*G06F 19/00* (2006.01)

(52) U.S. Cl. .......................... 702/19; 702/27
(58) Field of Classification Search .................. 702/19, 702/22
See application file for complete search history.

(56) References Cited

OTHER PUBLICATIONS

Karplus, P. A. Protein Science, 6, 1997, p. 61302-61307.*
Eisenberg et al., "Hydrophobic Moments and Protein Structure," Faraday Symp. Chem. Soc., 17:109-120 (1982).
Felts et al., "Distinguishing Native Conformations of Proteins from Decoys with an Effective Free Energy Estimator Based on the OPLS All-Atom Force Field and the Surface Generalized Born Solvent Model," Proteins: Structure, Function, and Genetics, 48:404-422 (2002).
Silverman, D.B., "Hydrophobic Moments of Protein Structures: Spatially Profiling the Distribution," Columbia University, Proc. Nat'l Acad. Sci. U.S.A. 98, 4996-5001 (2001).
Silverman, D.B., "A Two-Component Nucleation Model of Protein Hydrophobicity," J. Theor. Biol., 216:139-146 (2002).
Zhou et al., "Detecting Native Protein Folds Among Large Decoy Sets with Hydrophobic Moment Profiling," Proceedings of Pacific Symposium on Biocomputing 2002, Eds. R.B. Altman, A.K. Dunker, L. Hunter, K. Lauderdale and T.E. Klein, 673-684, World Scientific, Singapore (2002).

* cited by examiner

*Primary Examiner*—Michael Borin
(74) *Attorney, Agent, or Firm*—Ryan, Mason & Lewis, LLP

(57) ABSTRACT

Techniques for analyzing one or more protein structures. In one aspect of the invention, the technique comprises the following steps. A normalized second-order hydrophobic moment is determined for a protein structure. The normalized second-order hydrophobic moment is then used for analysis of the protein structure. A scoring function in accordance with the normalized second-order hydrophobic moment for the protein structure may be determined. A score for the protein structure may then be generated using the scoring function. The scoring function may represent an integral of the normalized second-order hydrophobic moment. The scores may be generated for a plurality of protein structures. The scores generated for the plurality of protein structures may then be compared.

7 Claims, 21 Drawing Sheets

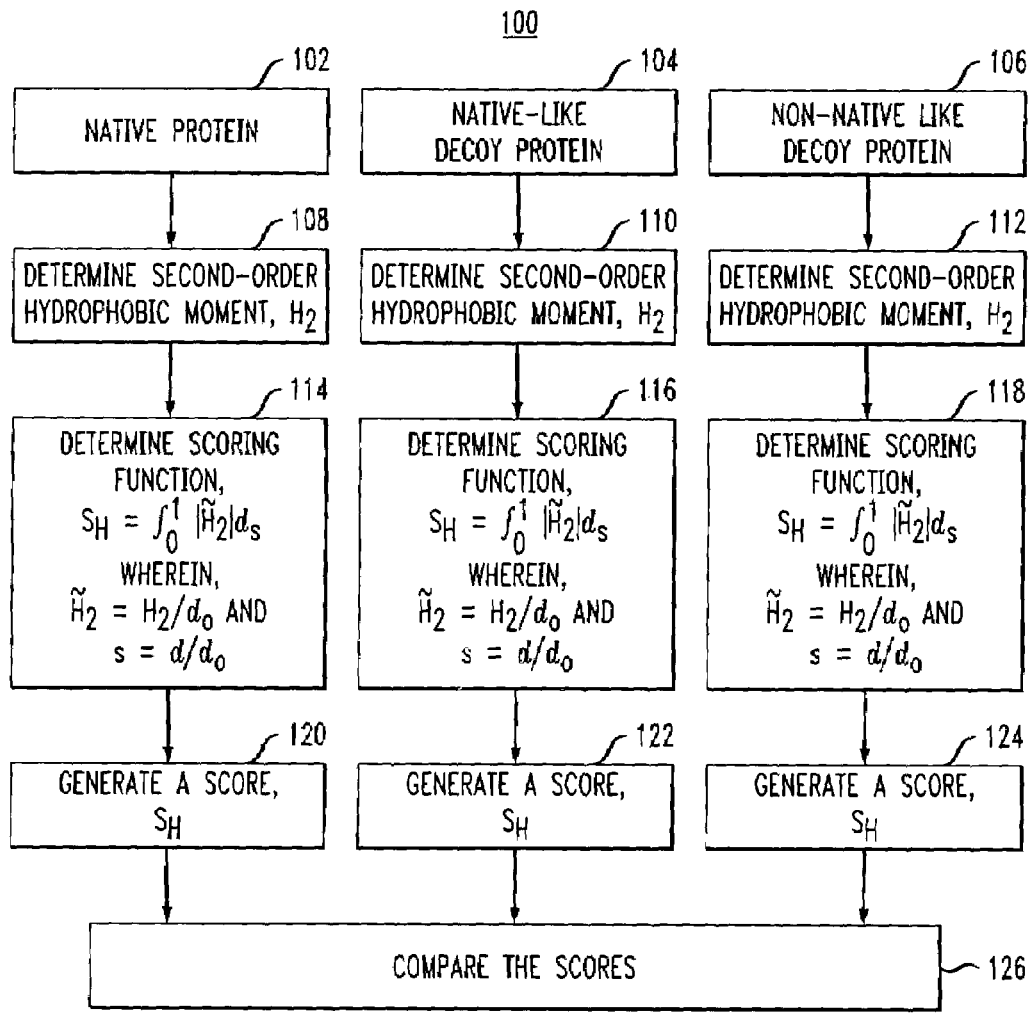
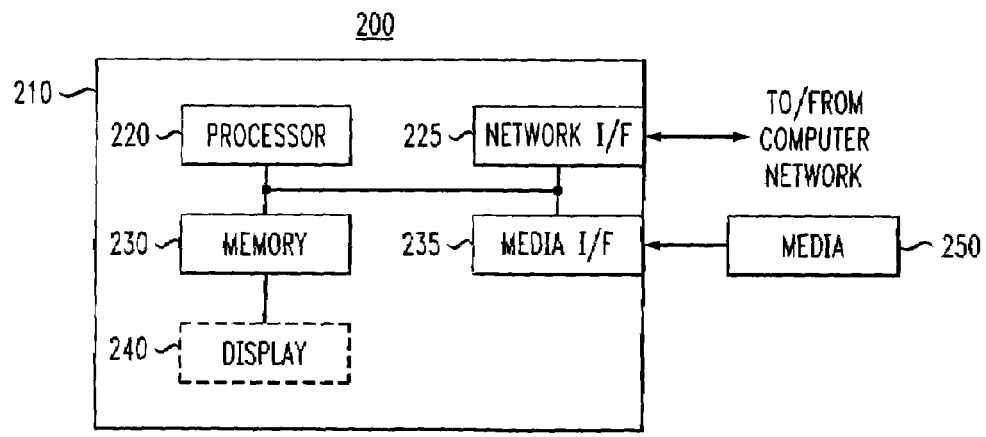

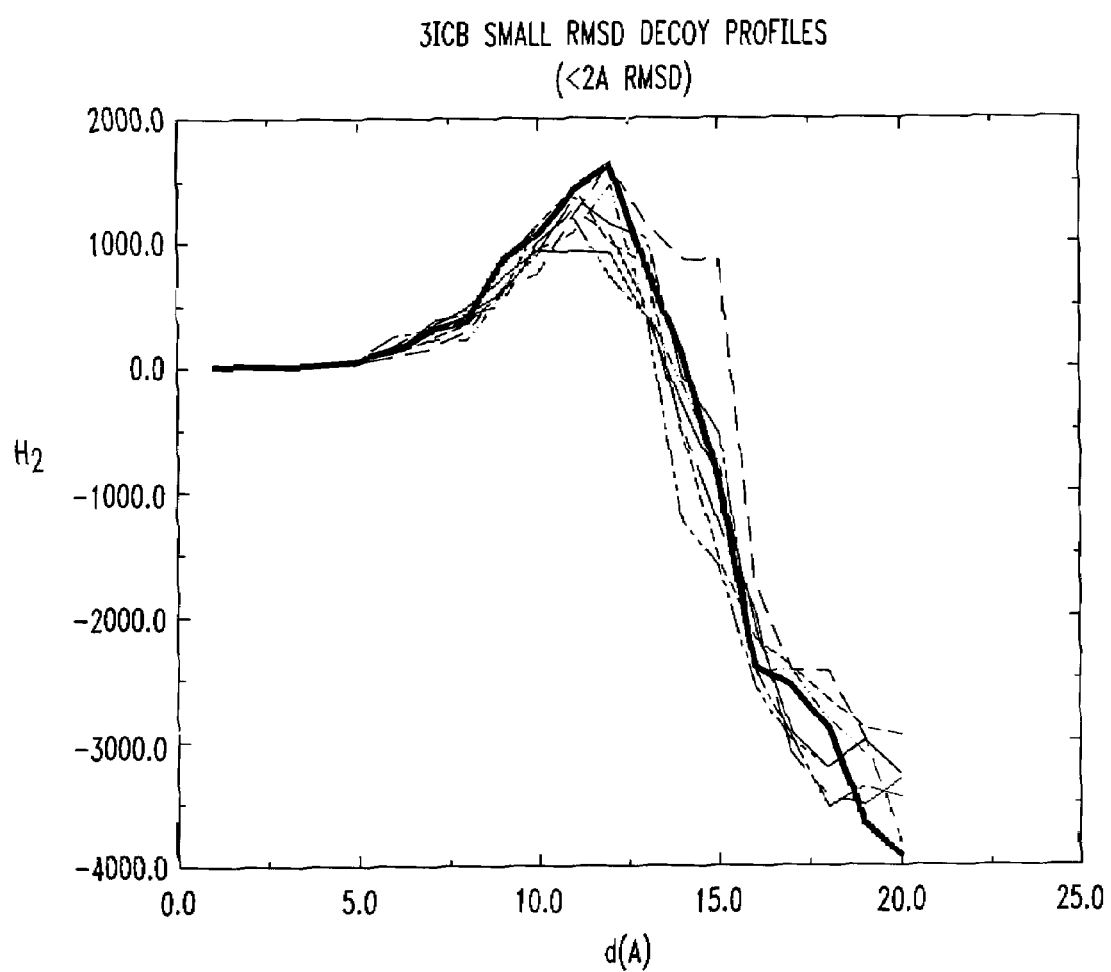

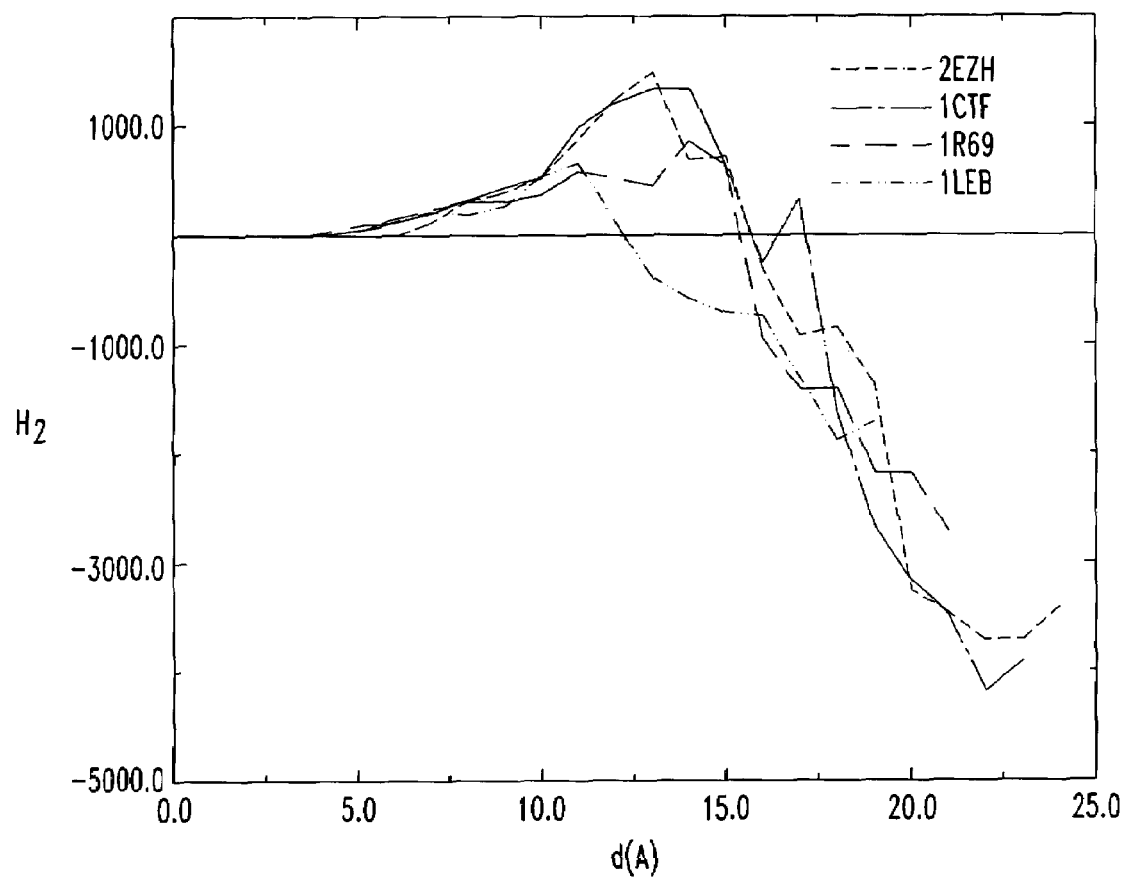

METHOD AND APPARATUS FOR PROTEIN STRUCTURE ANALYSIS

FIELD OF THE INVENTION

The present invention relates to structure analysis and, more particularly, to protein structure analysis using a scoring function.

BACKGROUND OF THE INVENTION

Proteins are composed of a series of amino acid residues. There are 20 naturally occurring amino acids. The three-dimensional structure of a protein typically comprises a series of folded regions. When profiling a protein, researchers attempt to determine the amino acid spatial order and location in three-dimensional space. The profiling of a protein is important because many of the functions associated with the human body depend on the particular protein structure.

Many proteins are globular and form in an aqueous environment. These globular proteins comprise hydrophobic amino acids that repel water, and hydrophilic amino acids that are attracted to water. When these proteins fold up, the hydrophobic amino acids are predominantly arranged in the non-aqueous center of the protein molecule and the hydrophilic amino acids are arranged on the aqueous protein surface. A protein formed in this manner will have a hydrophobic core and a hydrophilic exterior.

Of use in the study of protein structure is the ability to compare different structures. Decoy proteins have been developed to test the effectiveness of structure analysis methods. Decoy proteins are man-made protein structures that may be derived from naturally occurring proteins, but possess structural deviations. Decoy proteins can be used to test the sensitivity and effectiveness of structure analysis methods. For example, decoy proteins may be disbursed within a test set of proteins and the effectiveness of the analysis will be reflected by the identification of all the decoy proteins. Some commonly used protein decoys include the Holm & Sander decoys, the Park & Levitt decoys and the Baker decoys. A single native, i.e., naturally occurring, protein may be used to generate numerous decoy proteins. Therefore, any given set may comprise thousands of decoy proteins.

Accordingly, given such a large number of protein structures, effective techniques for comparing such protein structures would be desirable. Further, it would be desirable if such comparison could be performed for a plurality of structures.

SUMMARY OF THE INVENTION

The present invention provides techniques for analyzing one or more protein structures. In one aspect of the invention, the technique comprises the following steps. A normalized second-order hydrophobic moment is determined for a protein structure. The normalized second-order hydrophobic moment is then used for analysis of the protein structure.

A scoring function in accordance with the normalized second-order hydrophobic moment for the protein structure may then be determined. A score for the protein structure may then be generated using the scoring function. The scoring function may represent an integral of the normalized second-order hydrophobic moment. The scores may be generated for a plurality of protein structures. The scores generated for the plurality of protein structures may then be compared.

A more complete understanding of the present invention, as well as further features and advantages of the present invention, will be obtained by reference to the following detailed description and drawings.

BRIEF DESCRIPTION OF THE DRAWINGS

FIG. 1 is a flow chart illustrating an exemplary methodology for analysis of a protein structure according to an embodiment of the present invention;

FIG. 2 is a block diagram of an exemplary hardware implementation of a method for comparing protein structures according to an embodiment of the present invention;

FIG. 4 is a plot showing the second-order hydrophobic moment of decoys with a small Root Mean Square Deviation (RMSD);

FIG. 10 is a plot showing second-order hydrophobic moments for the four native proteins in the Baker decoy set;

DETAILED DESCRIPTION OF PREFERRED EMBODIMENTS

Figure 3A:
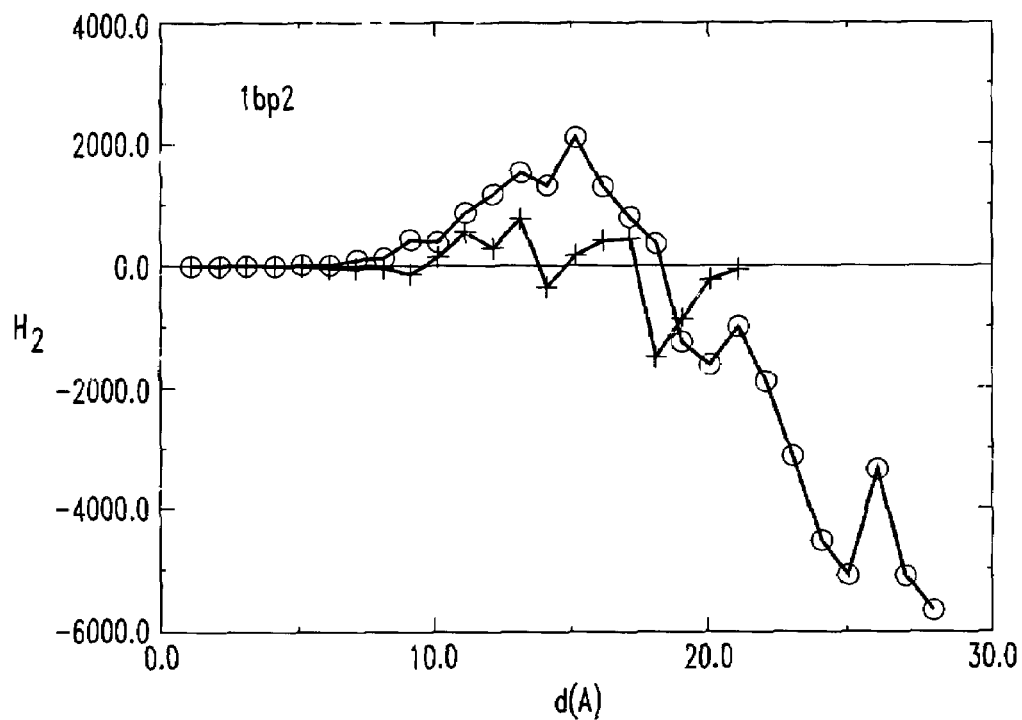
FIGS. 3(A)-(N) are plots showing the second-order moments for the native and decoy proteins of the Holm & Sander decoy sets.
Figure 3B:
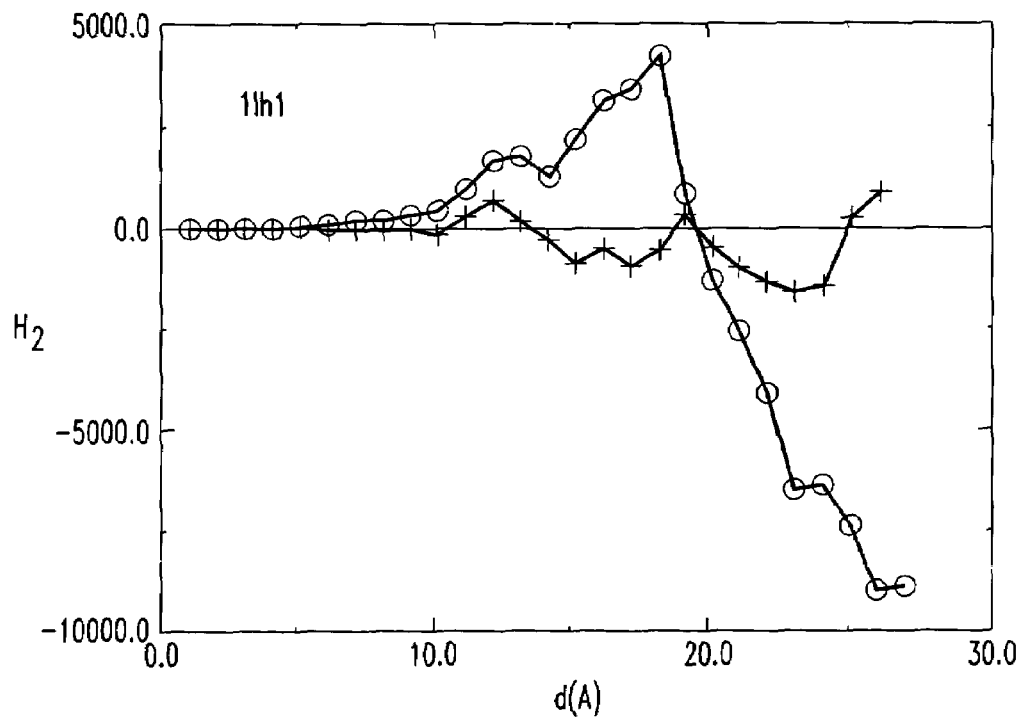
Figure 3C:
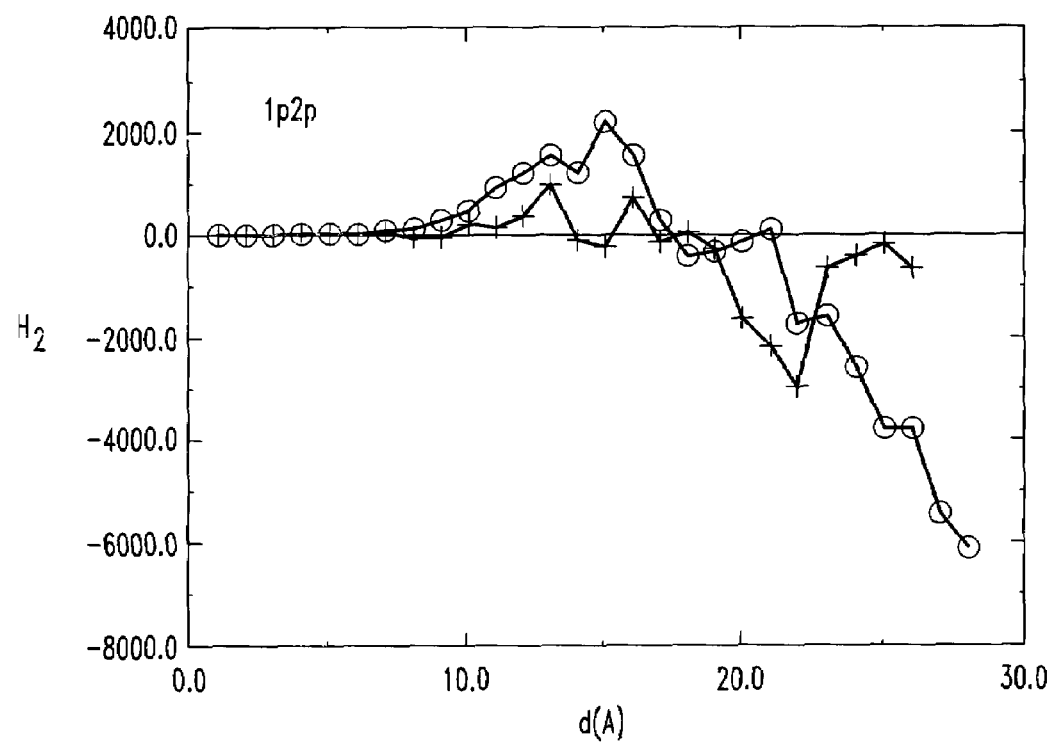
Figure 3D:
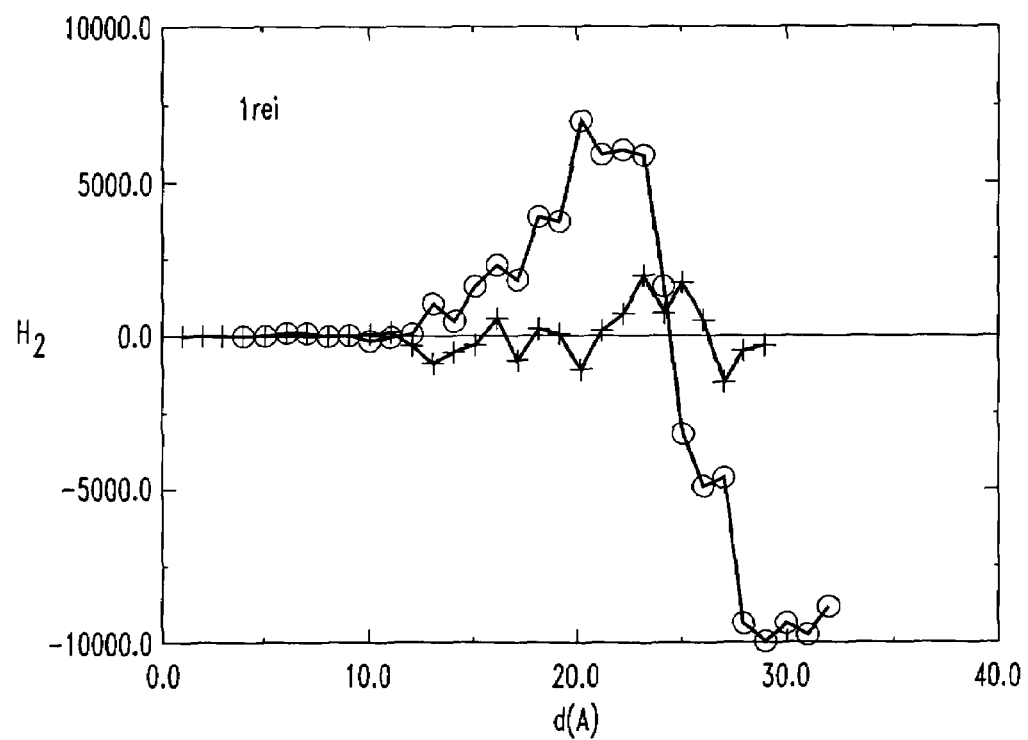
Figure 3E:
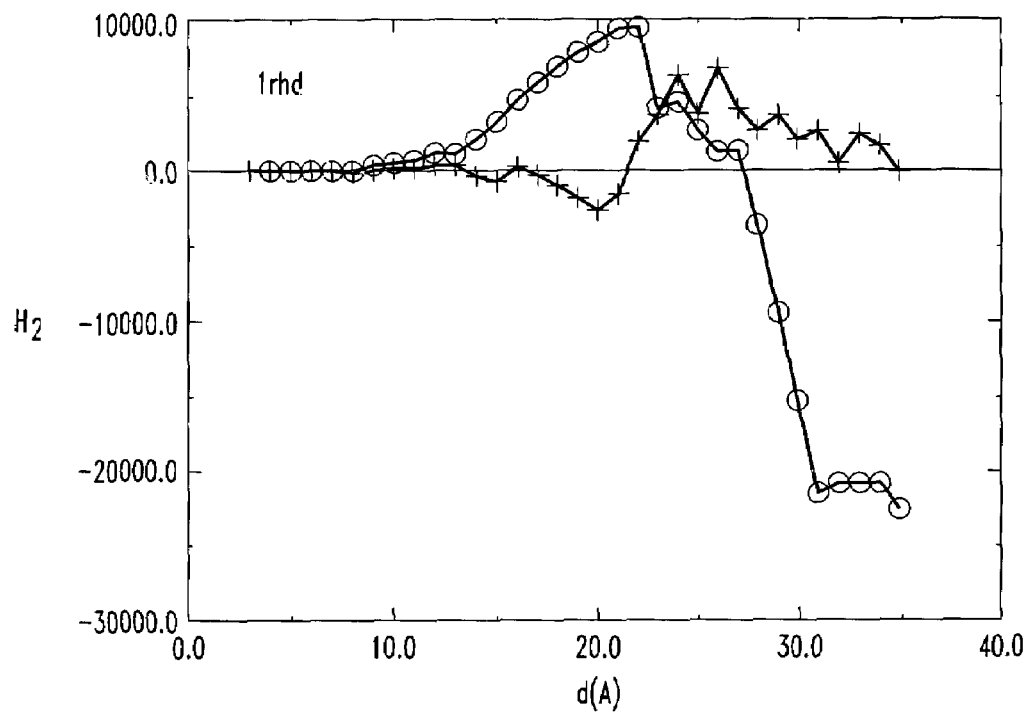
Figure 3F:
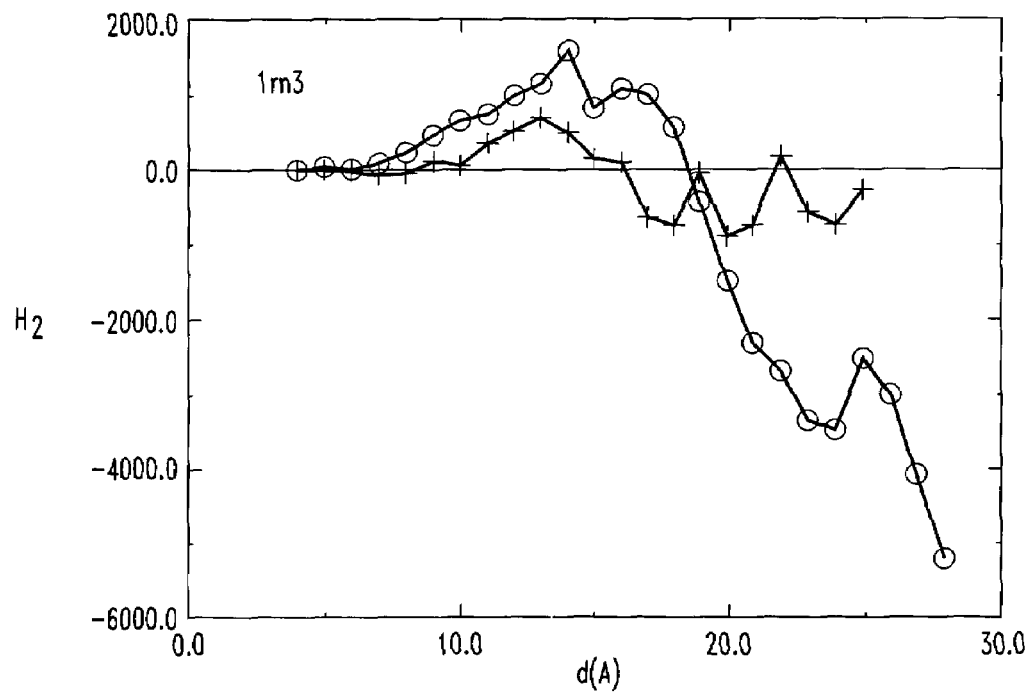
Figure 3G:
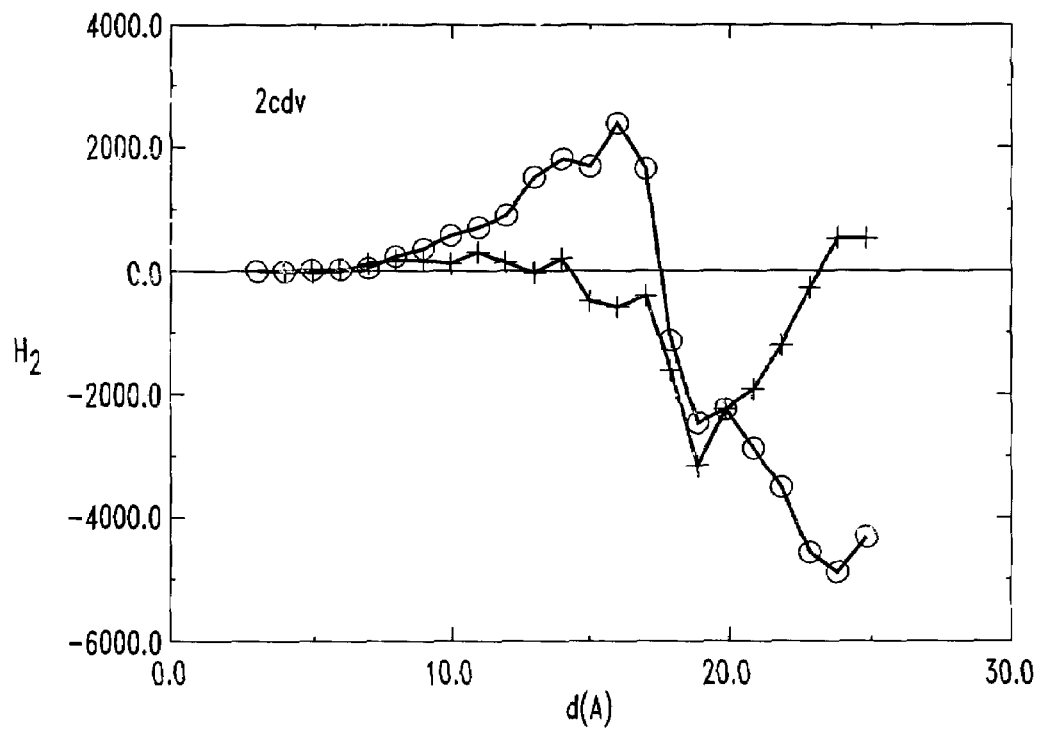
Figure 3H:
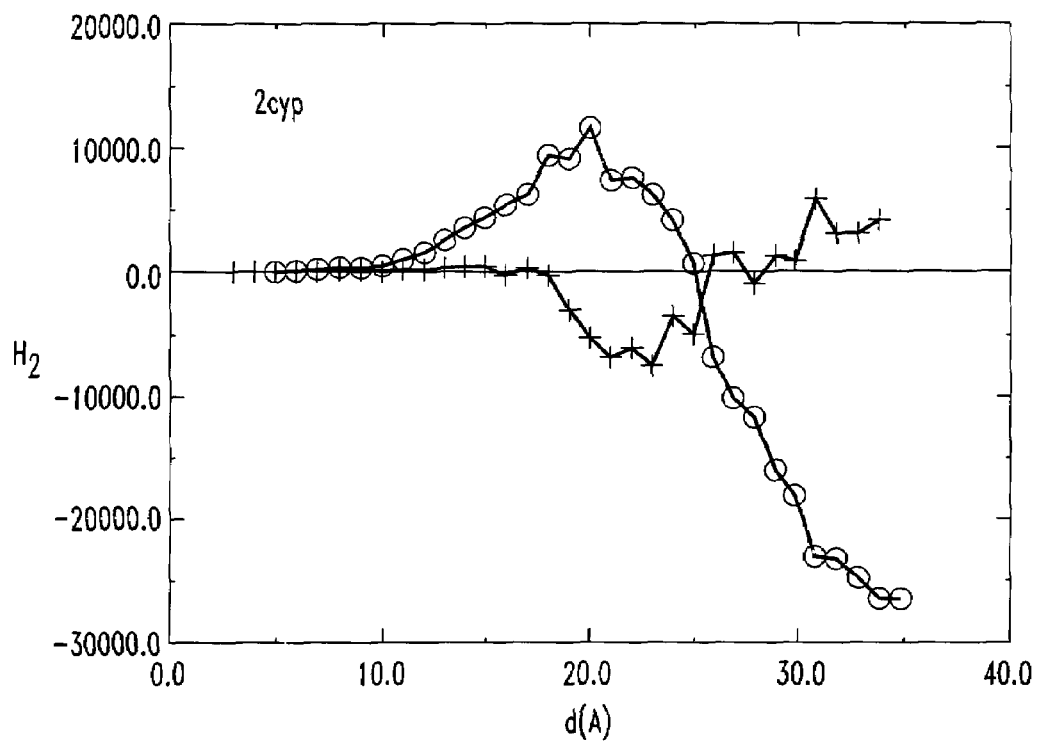
Figure 3I:
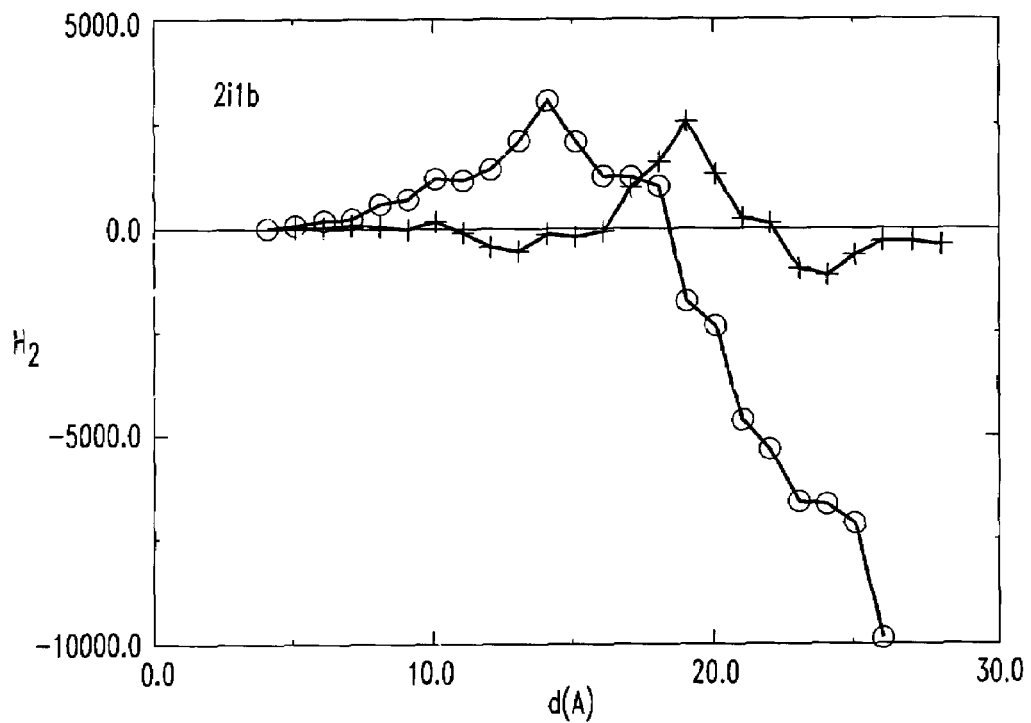
Figure 3J:
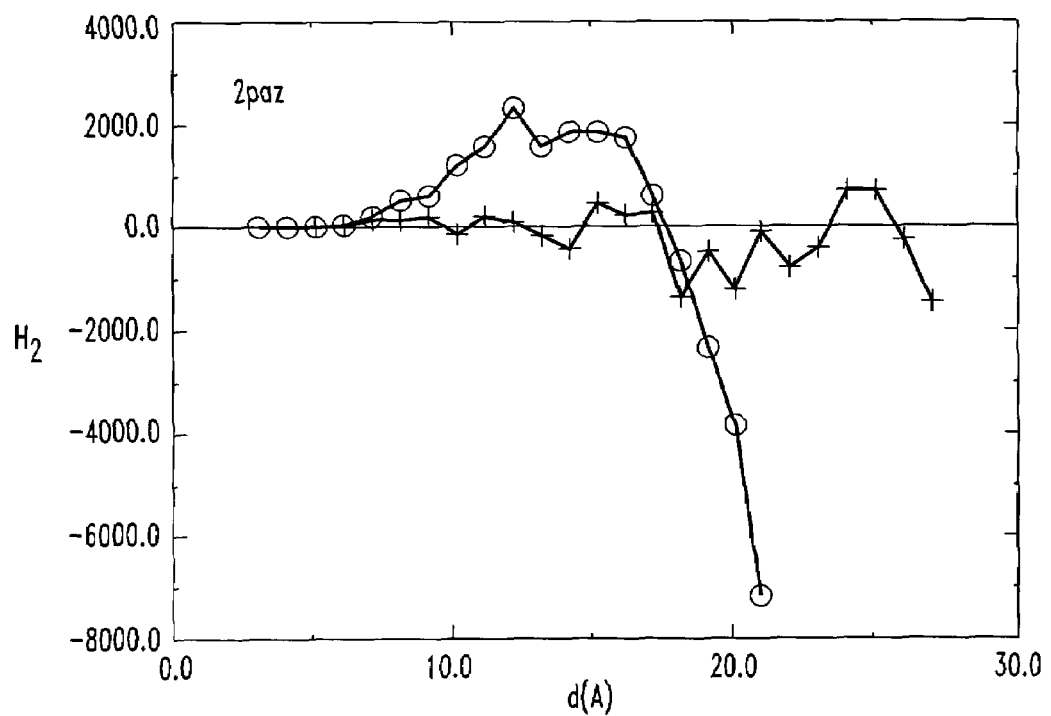
Figure 3K:
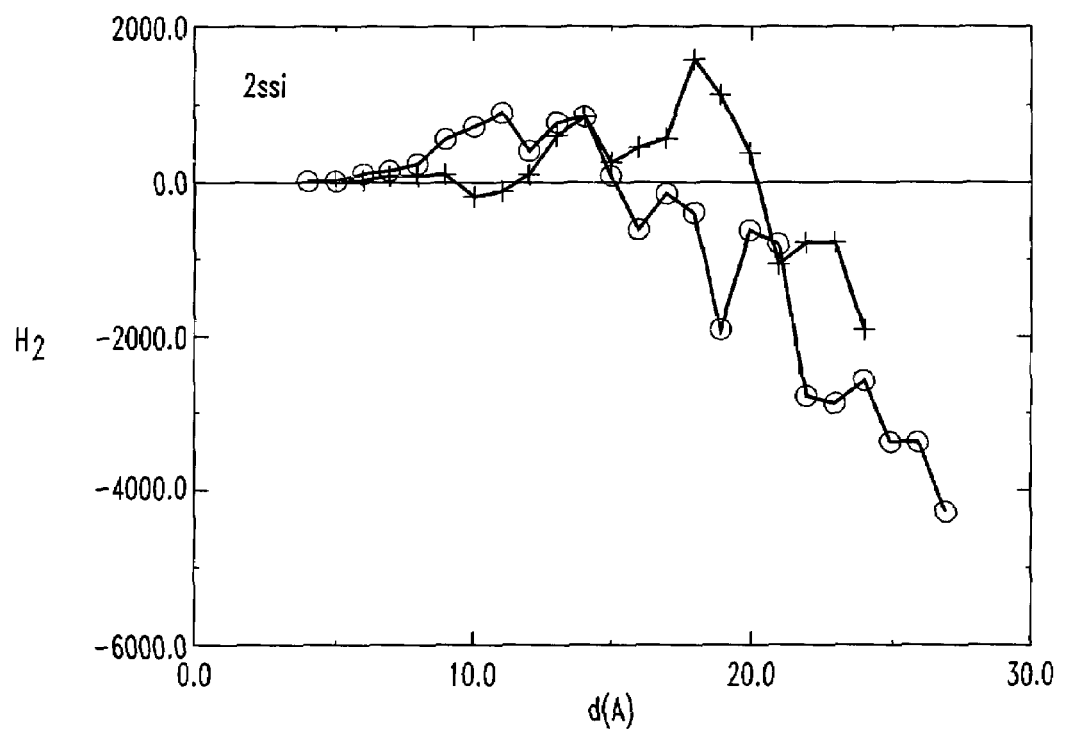
Figure 3L:
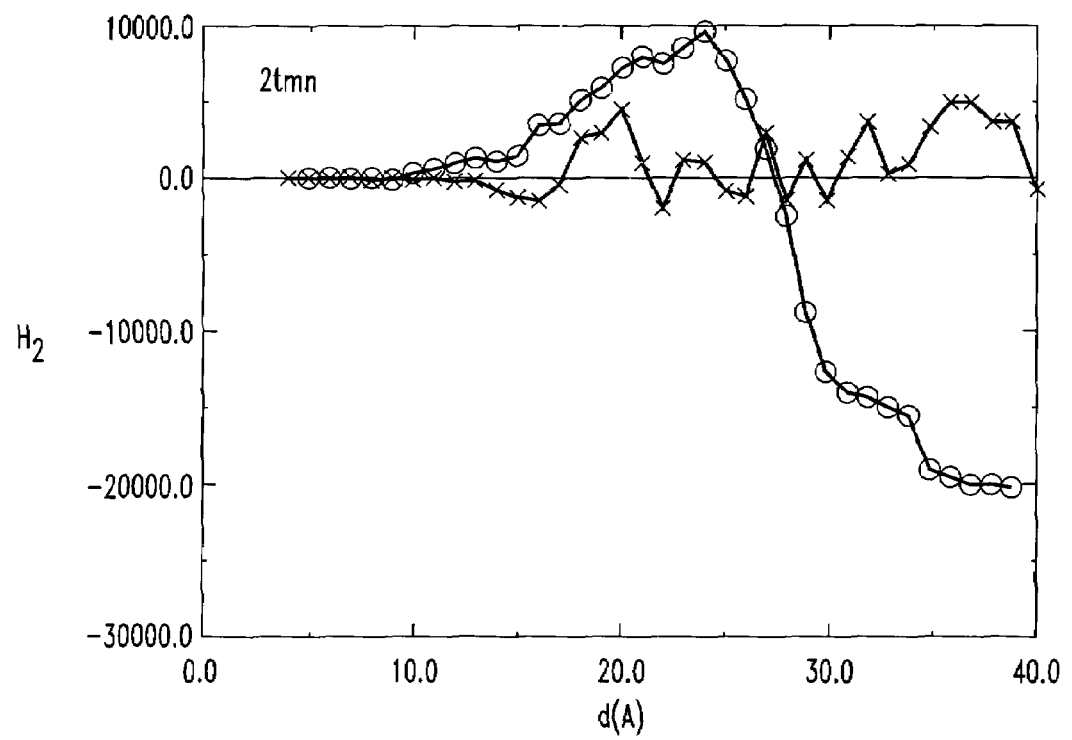
Figure 3M:
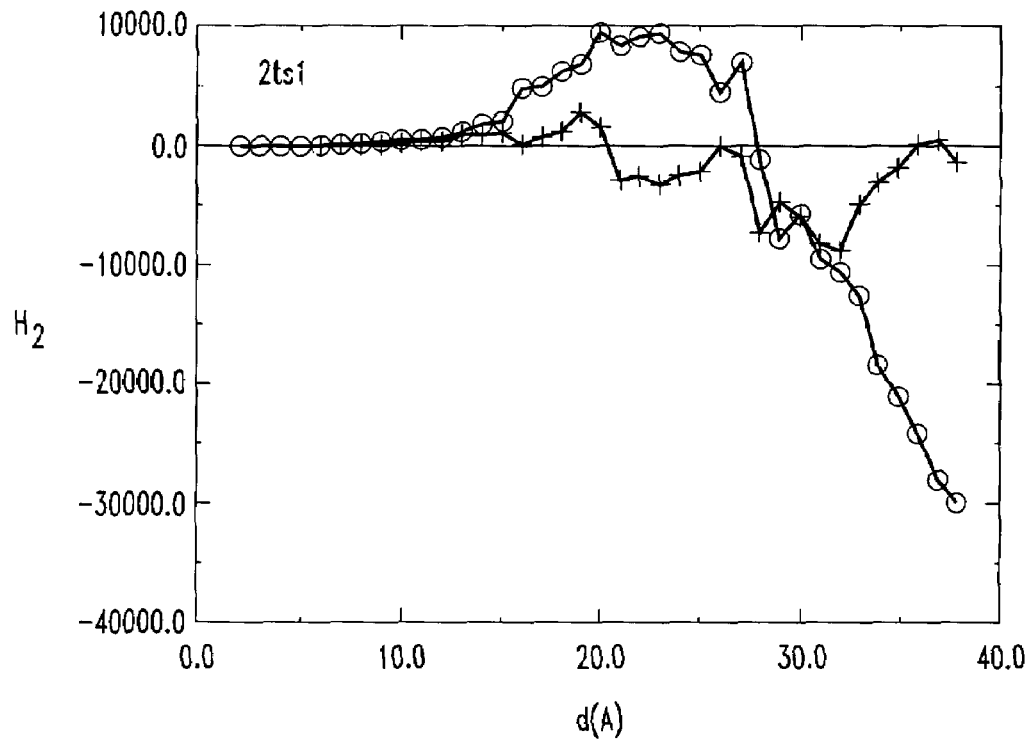

The present invention will be described below in the context of an illustrative analysis of a protein structure. However, it is to be understood that the present invention is not limited to such a particular protein structure analysis. Rather, the invention is more generally applicable to any protein structure analysis. Further, while the analysis of a protein structure will be described, the teachings of the present invention should not be construed as being limited to the analysis of proteins.

FIG. 1 is a flow chart illustrating an exemplary methodology 100 for the analysis of a protein structure. Preferred protein structures include, but are not limited to, native proteins 102 and two types of decoy proteins, namely, native-like decoy proteins 104 and non-native-like decoy proteins 106. Many decoy proteins are derived from a native protein. As such, some decoy proteins have a structure more closely resembling the native protein from which they are derived than do other decoy proteins. Native-like decoy proteins 104 are decoy proteins that have structures with Root Mean Square Deviation (RMSD) values within about three angstroms (Å) from the native protein. Non-native-like decoy proteins 106 are decoy proteins that have structures with RMSD values that are greater.

For each of native proteins 102, native-like decoy proteins 104 and non-native-like decoy proteins 106, a normalized second-order hydrophobic moment, 108, 110 and 112, respectively, is determined. The determination of a normalized second-order hydrophobic moment will be described in more detail in section (I) Hydrophobic Profiling, below. Normalized second-order hydrophobic moments 108, 110 and 112 are then used to determine scoring functions 114, 116 and 118, respectively. The determination of a scoring function will be described in more detail in section (III) Hydrophobic Scoring, below. Scoring functions 114, 116 and 118 are then used to generate scores (denoted as $S_H$) 120, 122 and 124, respectively. Scores 120, 122 and 124 may then be compared. The generation of a score, $S_H$, using a scoring function, and the comparison of scores will also be described in more detail in section (III) Hydrophobic Scoring, below.

FIG. 2 is a block diagram of an exemplary hardware implementation of a method for analysis of a protein structure in accordance with one embodiment of the present invention. It is to be understood that apparatus 200 may implement methodology 100 described above. Apparatus 200 comprises a computer system 210 that interacts with media 250. Computer system 210 comprises a processor 220, a network interface 225, a memory 230, a media interface 235 and an optional display 240. Network interface 225 allows computer system 210 to connect to a network, while media interface 235 allows computer system 210 to interact with media 250, such as a Digital Versatile Disk (DVD) or a hard drive.

As is known in the art, the methods and apparatus discussed herein may be distributed as an article of manufacture that itself comprises a computer-readable medium having computer-readable code means embodied thereon. The computer-readable program code means is operable, in conjunction with a computer system such as computer system 210, to carry out all or some of the steps to perform the methods or create the apparatus discussed herein. The computer-readable code is configured to determine a normalized second-order hydrophobic moment for a protein structure and to use the normalized second-order hydrophobic moment for analysis of the protein structure. The computer-readable medium may be a recordable medium (e.g., floppy disks, hard drive, optical disks such as a DVD, or memory cards) or may be a transmission medium (e.g., a network comprising fiber-optics, the world-wide web, cables, or a wireless channel using time-division multiple access, code-division multiple access, or other radio-frequency channel). Any medium known or developed that can store information suitable for use with a computer system may be used. The computer-readable code means is any mechanism for allowing a computer to read instructions and data, such as magnetic variations on a magnetic medium or height variations on the surface of a compact disk.

Memory 230 configures the processor 220 to implement the methods, steps, and functions disclosed herein. The memory 230 could be distributed or local and the processor 220 could be distributed or singular. The memory 230 could be implemented as an electrical, magnetic or optical memory, or any combination of these or other types of storage devices. Moreover, the term "memory" should be construed broadly enough to encompass any information able to be read from or written to an address in the addressable space accessed by processor 220. With this definition, information on a network, accessible through network interface 225, is still within memory 230 because the processor 220 can retrieve the information from the network. It should be noted that each distributed processor that makes up processor 220 generally contains its own addressable memory space. It should also be noted that some or all of computer system 210 can be incorporated into an application-specific or general-use integrated circuit.

Optional video display 240 is any type of video display suitable for interacting with a human user of apparatus 200. Generally, video display 240 is a computer monitor or other similar video display.

For ease of reference, the following description will be divided into the following sections; (I) Hydrophobic Profiling, (II) Decoy Proteins and (III) Hydrophobic Scoring. Hydrophobic profiling is presented first to provide a basis for the discussion of decoy proteins and hydrophobic scoring.

I. Hydrophobic Profiling

It is to be understood that the following description exemplifies the determination of a normalized second-order hydrophobic moment as referred to in conjunction with the determination of normalized second-order hydrophobic moments 108, 110 and 112 of FIG. 1. The analysis of a protein structure typically involves the comparison of that structure to numerous other protein structures, with varying degrees of structural similarities. The analysis becomes increasingly more difficult as the number of structures being compared increases. One way researchers have tried to overcome this hurdle is by identifying similarities between structures. One area researchers have focused on is the hydrophobic profile of protein structures.

Hydrophobicity, a characteristic of the hydrophobic profile, is widely used to describe the solvation of small organic molecules, proteins, or other molecules in a water solvent. For proteins, each amino acid residue making up the protein exhibits a different degree of hydrophobicity or hydrophilicity based on its solubility in water. A value of hydrophobicity, $h_i$, can be assigned to each amino acid residue of type, i. Table 1, as shown below, lists the Eisenberg hydrophobicity consensus values for each naturally occurring amino acid residue.

TABLE 1

| Amino Acid residue | Residue hydrophobicity |
|---|---|
| Arginine | −1.76 |
| Lysine | −1.10 |
| Aspartic Acid | −0.72 |
| Glutamine | −0.69 |
| Asparagine | −0.64 |
| Glutamic Acid | −0.62 |
| Histidine | −0.40 |
| Serine | −0.26 |
| Threonine | −0.18 |
| Proline | −0.07 |
| Tyrosine | 0.02 |
| Cysteine | 0.04 |
| Glycine | 0.16 |
| Alanine | 0.25 |
| Methionine | 0.26 |
| Tryptophan | 0.37 |
| Leucine | 0.53 |
| Valine | 0.54 |
| Phenylalanine | 0.61 |
| Isoleucine | 0.73 |

With globular proteins, the distribution of hydrophobicity is profiled from the protein interior to the protein exterior. As such, an ellipsoidal profiling shape may be chosen with axes determined by the inertial tensor $\overline{\overline{I}}$, which has components:

$$I_{jk} = \int_V \rho(\vec{r})(r^2 \delta_{jk} - x_j x_k) dV,$$

where $\rho(\vec{r})$ is the density of the amino acid residue centroids of unit mass, r is the radial distance from the center of the ellipsoidal profiling shape, $x_j$ is the jth Cartesian coordinate, dV is the volume element in which the integral is performed, and $\delta_{jk}$ is the Dirac delta function with value of one, if j=k, and zero, otherwise. The three principal axes as well as the moments of geometry are obtained by diagonalizing the inertial tensor. The x, y and z axes are then aligned with the principal axes. The moments of geometry are designated as $g_1$, $g_2$ and $g_3$, with $g_1 < g_2 < g_3$. The ellipsoidal representation generated by these moments is:

$$x^2 + g'_2 y^2 + g'_3 z^2 = d^2$$

wherein $g'_2 = g_2/g_1$, $g'_3 = g_3/g_1$. The value d is the major principal axis of the ellipsoid and can be considered as a generalized ellipsoidal radius.

The hydrophobicity distribution is shifted such that the net hydrophobicity of each protein vanishes, regardless of the initial distribution of the amino acid residue hydrophobicity, $h_i$. The distribution is then normalized to yield a standard deviation of one. Shifting the amino acid residue hydrophobicity distribution for each protein selects a common structural reference and thus enables the quantitative comparison of protein profile shapes and profile features such as the hydrophobic ratio.

The hydrophobic ratio, a relatively universal constant, is the ratio of radii from the protein centroid at which the second-order hydrophobic moment and the zero-order moment vanishes. The protein centroid is defined as the centroid of the amino acid residue centroids, that make up the protein. The centroid of an amino acid residue is the center of mass of the residue, when each atom of the residue is assigned a location with a mass value of one. A recent study of thirty globular protein structures revealed a relative constant hydrophobic ratio of 0.75±0.05 for thirty protein structures. A general description of the hydrophobic profiling of proteins, including the determination of the hydrophobic ratio, is provided in U.S. patent application Ser. No. 09/818,461, filed Mar. 27, 2001, entitled "Spatial Profiling of Proteins Using Hydrophobic Moments," incorporated herein by reference.

A zero-order hydrophobic moment $H_0$ of the residue distribution within the ellipsoidal surface specified by d is written as:

$$H_0(d) = \sum_{r<d} h'_i = \sum_{r<d} (h_i - \overline{h}) / \langle (h_j - \overline{h})^2 \rangle^{1/2}$$

wherein r represents the radius, the prime designates the value of hydrophobicity of each residue after shifting and normalizing the distribution, wherein $\overline{h}$ is the mean of the $h_i$, and $\langle (h_j - \overline{h})^2 \rangle^{1/2}$ represents the standard deviation. At the ellipsoidal surface, all proteins have a total hydrophobicity value of zero, i.e., each residue has a hydrophobicity value of zero. This point may be used as a reference for comparing different proteins. Therefore, when the value of d is just large enough to collect all of the residues, the net hydrophobicity of the protein vanishes. This value of $d_0$, for which $H_0(d)$ vanishes assigns a surface as common structural reference for each protein.

Second-order hydrophobic moments amplify the differences between hydrophobic and hydrophilic amino acid residues that contribute to the hydrophobicity profile. The second-order hydrophobic moment $H_2$ is defined as:

$$H_2(d) = \Sigma h'_i (x_i^2 + g'_2 y_i^2 + g'_3 z_i^2),$$

wherein $(x_i, y_i, z_i)$ denotes the position of an amino acid residue centroid. For globular native proteins, the zero and second-order moments are positive when the distance, d, is small. Both the zero and second-order moments increase with distance, d, while in the region of the hydrophobic core. With increasing values of d from the core, the ratio of hydrophilic to hydrophobic amino acid residues increases. Eventually the zero and second-order moments begin decreasing with increasing distance, d. Since the second-order hydrophobic moment amplifies differences in the distribution, the second-order hydrophobic moment will cross zero at a distance $d_2$ and then become negative. The location at which the second-order hydrophobic moment vanishes is defined as $d_2$. The distance at which the zero-order hydrophobic moment vanishes is denoted as $d_0$. A hydrophobic ratio may then be defined as:

$$R_H = d_2/d_0$$

The hydrophobic ratio, however, cannot always be defined for arbitrary protein structures, such as decoy proteins, especially if the second-order moment profile does not exhibit the smooth, generic behavior expected from a native protein.

II. Decoy Proteins

Some decoy protein sets are available, i.e., on the worldwide web. Three decoy sets widely used by researchers are the Holm & Sander decoys, Park & Levitt decoys and Baker decoys. These three sets may be obtained from Stanford University (http://dd.stanford.edu) for the Holm & Sander and Park & Levitt sets and from the University of Washington (http://depts.washington.edu/bakerpg) for the Baker set. Since determining the hydrophobic moments and hydrophobic ratios of a protein structure involves the spatial profiling of the amino acid residue distribution, and since the amino acid residue distribution is discretely distributed in space, a typical window of one Å in generalized ellipsoidal radius, d, is used to generate the nested ellipsoidal surfaces. Choosing this parameter provides reasonable resolution in obtaining the generally smooth moment profiles over a range of protein sizes.

Since hydrophobic profiling characterizes a global feature and requires reasonably good statistics, a constraint is imposed on the size of the protein structures that yields relatively smooth moment profiles. A relatively smooth profile can be obtained for a protein with a large number of amino acid residues, i.e., the protein may comprise greater than or equal to about 60 amino acid residues. For example, the Holm & Sander decoys each have a reasonably large number of amino acid residues, i.e., 14 decoy sets out of 26 have proteins ranging from 107 to 317 amino acid residues. Thus, when using the Holm & Sander decoys, it is possible to choose only those decoys with greater than or equal to 100 amino acid residues. In contrast, the Park & Levitt or Baker decoy sets have, many decoys with less than 100 amino acid residues. Thus, when using decoys from either of these two sets, it is preferable to choose those decoys with greater than or equal to 60 amino acid residues. Typically, the decoys within each set are further organized into subsets. The subsets are based upon the native protein from which the subset was derived. The native protein may be obtained from a database, such as the Protein Databank (PDB Databank).

Additional limitations may also be imposed on the decoys chosen. For example, when Baker decoys are used, two further standards are applied to select subsets:

(1) those decoy subsets wherein less than or equal to 10 percent of the decoy proteins in the subset have RMSD values less than eight angstroms (as compared to the native protein) are eliminated; and (2) those decoy subsets wherein the decoys in the subsets have a smallest RMSD value larger than four angstroms (as compared to the native protein) are eliminated.

The objective is to select decoys with a broad range of RMSD values, and thus a broad range of similarity to the corresponding native proteins, to examine. However, decoy sets in which all decoys are significantly displaced in RMSD from the corresponding native proteins are eliminated.

Imposing the limitations described above eliminates 81 of the 92 Baker subsets. Imposing the limitation that decoys must have greater than or equal to 60 amino acid residues reduces the number of Park & Levitt subsets to 4, from a total of 7.

Table 2, shown below, contains the resulting decoy subsets from the Park & Levitt and Baker sets after the limitations have been imposed.

TABLE 2

| Decoy Set | PDB entry | # of Amino Acid Residues | Hydrophobic Ratio |
|---|---|---|---|
| Park & Levitt | 1ctf | 68 | 0.722 |
| | 1r69 | 63 | 0.762 |
| | 2cro | 65 | 0.722 |
| | 3icb | 75 | 0.750 |
| Baker | 1c5a | 62 | 0.727 |
| | 1ctf | 67 | 0.722 |
| | 1hsn | 62 | 0.679 |
| | 1leb | 63 | 0.684 |
| Baker | 1mzm | 67 | 0.773 |
| | 1nkl | 70 | 0.737 |
| | 1r69 | 61 | 0.762 |
| | 1sro | 66 | 0.640 |
| | 2ezh | 65 | 0.667 |
| | 2fow | 66 | 0.750 |
| | 2ptl | 60 | 0.682 |

The decoys shown in Table 2 have a range of from 60 to 75 amino acid residues. Although, many of the above decoys have a small number of amino acid residues and will not yield smooth second-order hydrophobic moment profiles, the hydrophobic profiling of these proteins can provide useful complementary information to that obtained from energy minimization procedures.

Figure 3N:
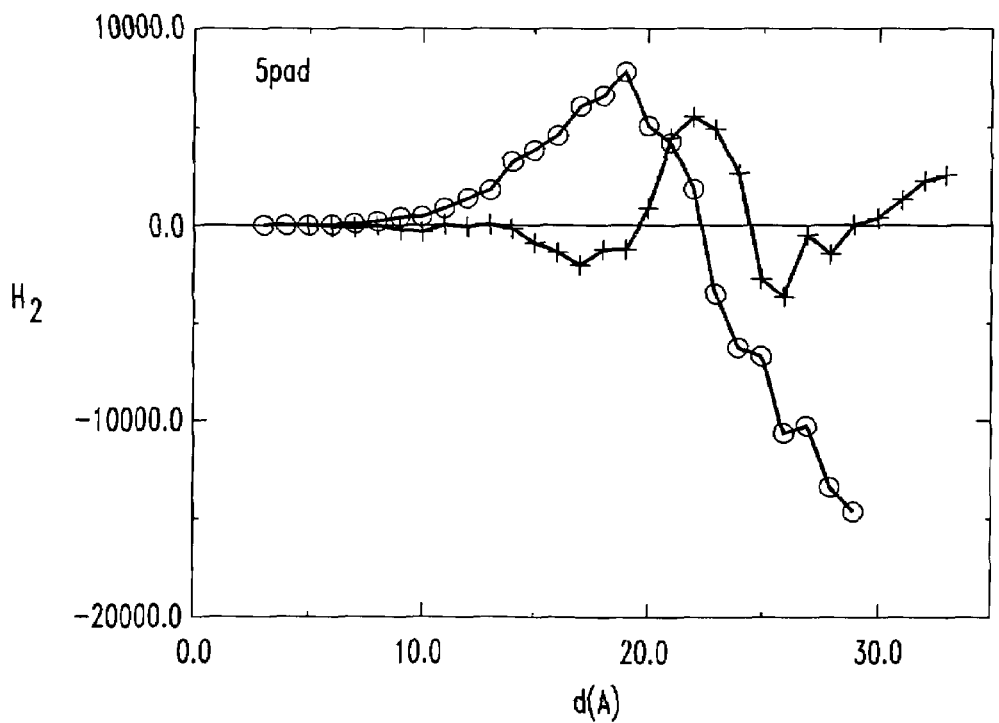

FIGS. 3(A)-(N) are plots showing the second-order hydrophobic moment profiles of 14 Holm & Sander decoys. Each plot characterizes one decoy and the corresponding native protein, wherein the native proteins are represented by circles and the decoys are represented by plus symbols, in each plot. All of the native proteins plotted show a second-order hydrophobic moment profile typical for native proteins. The second-order hydrophobic moment profiles for the decoy proteins, on the other hand, fluctuate around zero on the radial axis. Thus, a hydrophobic ratio cannot be defined for these decoy proteins.

III. Hydrophobic Scoring

It is to be understood that the following description exemplifies the determination of a scoring function and the comparison of scores as referred to in conjunction with the determination of scoring functions 114, 116 and 118 and comparing scores 120, 122 and 124, respectively, of FIG. 1. While the Holm & Sander decoys generally exhibit patterns that allow for the relatively easy comparison of structures, the second-order hydrophobic moment profiles of the thousands of Park & Levitt and Baker decoy structures do not always exhibit such patterns. Further, it is not feasible to visually or manually inspect the thousands of decoy profiles in the sets. Therefore, a scoring function is provided in accordance with the present invention to compare these profiles, and preferably to quantitatively rank the second-order hydrophobic moment profiles of each decoy with respect to the second-order hydrophobic moment profile of the corresponding native protein.

Figure 5:
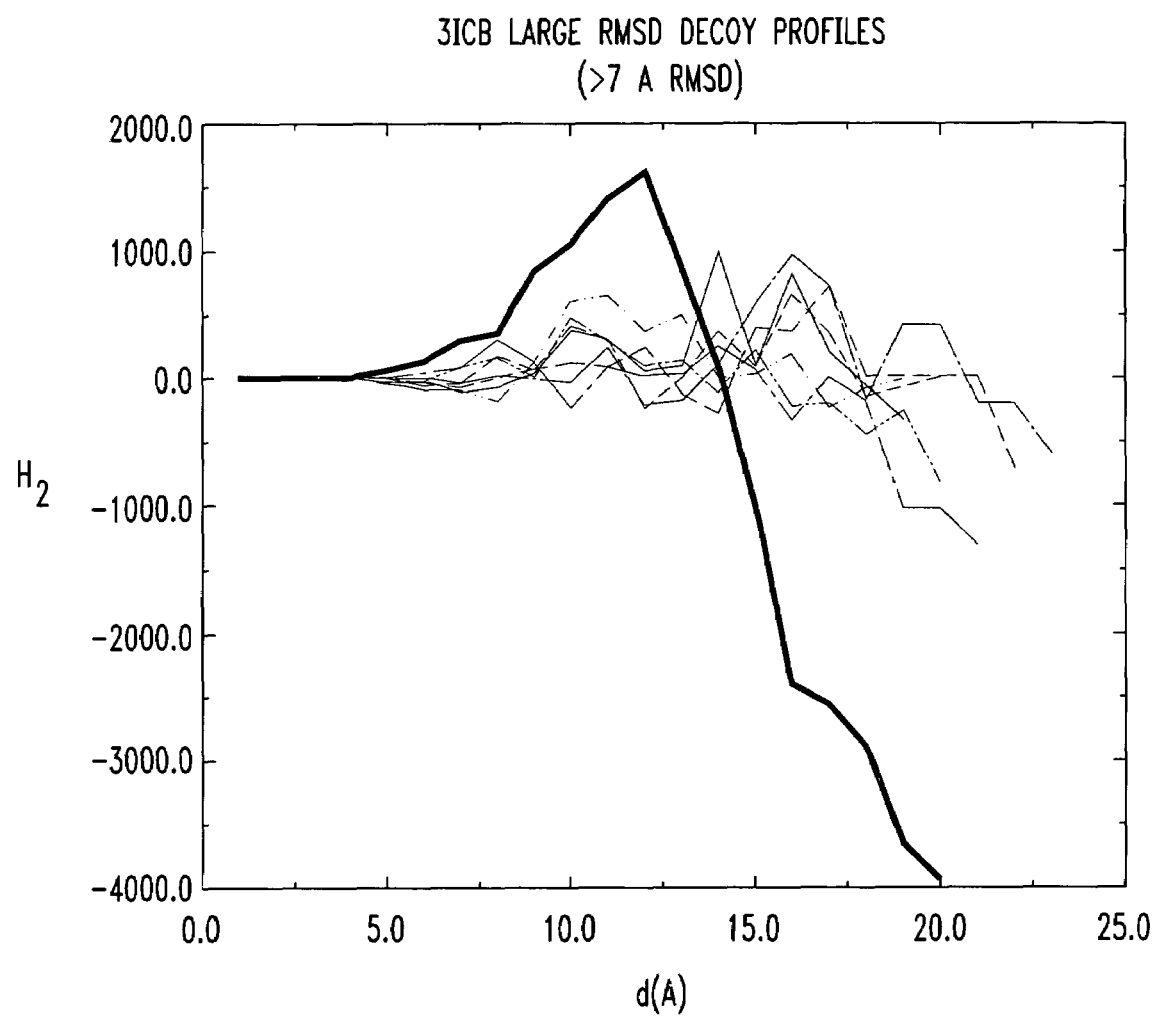
FIG. 5 is a plot showing the second-order hydrophobic moment of decoys with a large RMSD.
Figure 6A:
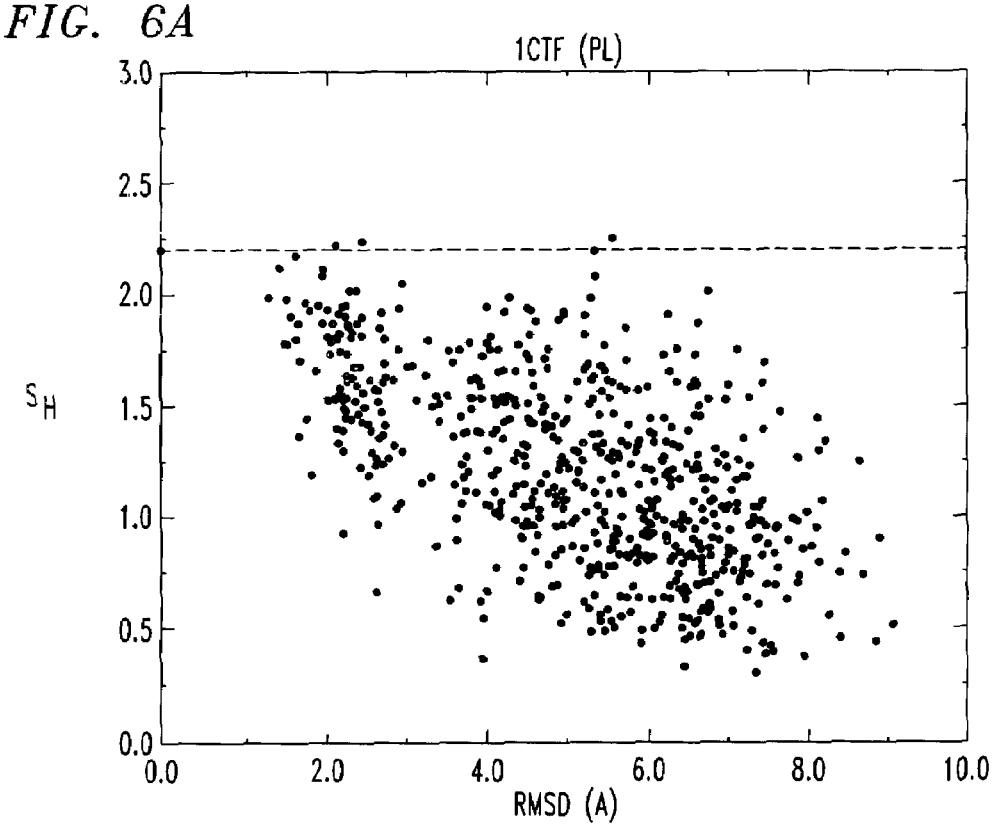
FIGS. 6(A)-(D) are plots showing the hydrophobic score ($S_H$) versus RMSD for the Park & Levitt decoys according to an embodiment of the present invention.
Figure 6B:
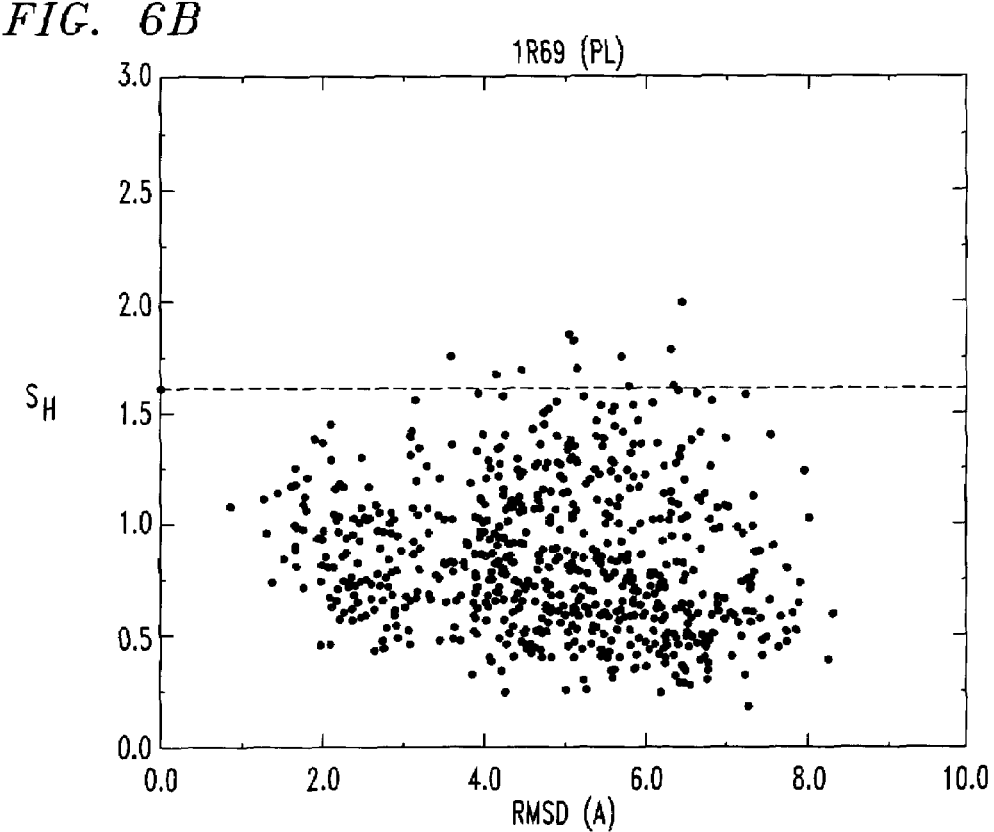
Figure 6C:
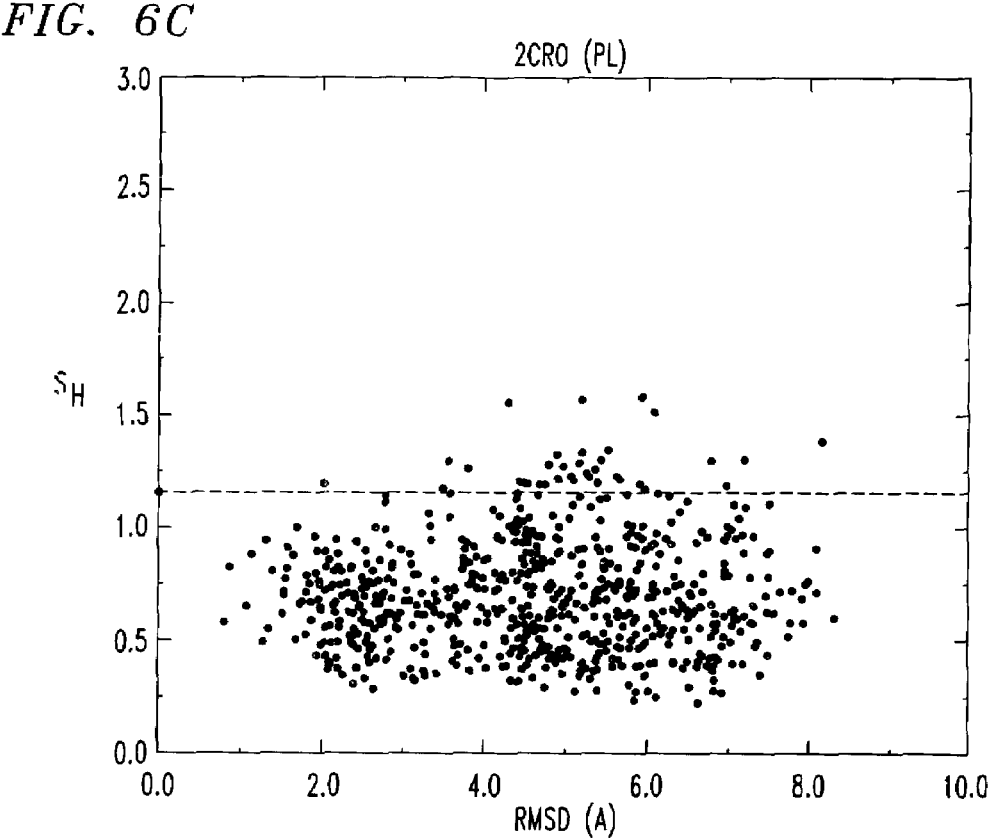
Figure 6D:
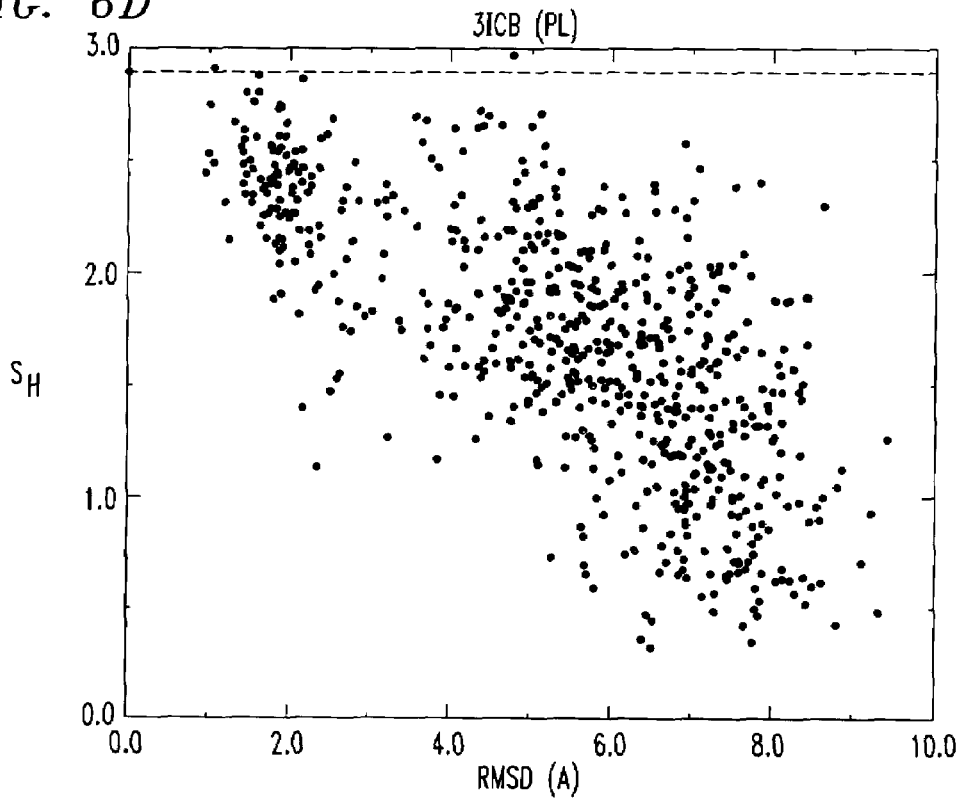

The examination of a few of the decoy profiles reveals several interesting features involved in defining the scoring function. FIG. 4 is a plot showing the second-order hydrophobic moment profile of decoys with a small RMSD, i.e., derived from native protein 3icb in the Park & Levitt decoy set with RMSD values less than 2 angstroms. The second-order hydrophobic moment profile of native protein 3icb is shown as the thick, dark curve for comparison. FIG. 5 is a plot showing the second-order hydrophobic moment profile of decoys with a large RMSD, i.e., derived from native protein 3icb in the Park & Levitt decoy set with RMSD values greater than seven angstroms. The second-order hydrophobic moment profile of native protein 3icb is again shown as the thick, dark curve for comparison.

The RMSD values provided are values for the $C_\alpha$ atoms. For those RMSD values which are not publicly available, e.g., for the Baker decoys, the RMSD values may be computed with the IMPACT program for all backbone atoms. Even though, the RMSD values will be slightly different if based on the $C_\alpha$ atoms, backbone atoms, or all of the atoms, the outcome does not significantly effect the analysis. The native-like structures show a second-order profile shape that mimics the native profile, which exhibits a strong hydrophobic core and a sharp plunge outside of the core approaching the hydrophilic exterior. The non-native-like decoy structures, on the other hand, do not show the significant separation between the hydrophobic core and hydrophilic exterior. The second-order hydrophobic moments of the non-native-like decoys also fluctuate about zero on the radial axis. Thus, the hydrophobic ratio cannot be easily defined, if at all possible.

The examination of decoy and native structure second-order hydrophobic moment profiles for an additional number of decoy sets reveals similar results. The second-order hydrophobic moment profiles for the native-like decoys exhibit a pronounced hydrophobic peak and a significant plunge to negative values outside the hydrophobic core, while the non-native-like decoys show a reduced hydrophobic peak and less prominent hydrophilic exterior. The second-order hydrophobic moment profiles of the decoy structures were also found to extend a greater distance from the centroid, than that which occurred in the second-order hydrophobic moment profiles of the corresponding native protein.

The total area under the second-order hydrophobic moment profiles (the area under both the hydrophobic peak and above the hydrophilic plunge) for the native proteins may be compared to the total area under the second-order hydrophobic moment profiles for the decoy proteins to discriminate the native proteins from the decoy proteins. However, a significant increase in protein extent of the decoy proteins could yield a spurious contribution from the area under the negative moment profile. Differences due to this contribution can be reduced, or eliminated, by scaling the native proteins and decoy proteins by the value of the decoy protein extent, $d_0$. The abscissa on the moment plot may be thus divided by $d_0$ and the second-order moment divided by $d_0^2$. Such scaling does not take any of the differences in amino acid residue number into account. For the present case, however, the decoys and their corresponding native proteins have the same number of amino acid residues.

While the description highlights the comparison of decoy proteins and native proteins, it is to be understood that the teachings of the present invention are not to be limited to such a specific application. For example, the methods provided herein are equally applicable to the comparison of multiple native proteins, and similarly to the comparison of multiple decoy proteins or any combination thereof.

The hydrophobic score, $S_H$, which ranks the quality of the decoy proteins with respect to a native protein, is then chosen as the integral of the area under the normalized second-order hydrophobic moment profiles of the native protein and the decoy protein:

$$\tilde{H}_2 = H_2/d_0^2$$

$$s = d/d_0$$

The absolute value of $\tilde{H}_2$ is integrated over the normalized distance, from 0 to 1:

$$S_H = \int_0^1 |\tilde{H}_2| ds$$

Score $S_H$ not only measures the prominence of the hydrophobic core, but also the prominence of the hydrophilic exterior. Score $S_H$ takes into account the rapidity of decrease of the second-order hydrophobic moment profile outside of the hydrophobic core.

FIGS. 6(A)-(D) are plots showing $S_H$ versus RMSD values for four Park & Levitt decoy sets that meet the limitations highlighted above (in section II). The dashed lines indicate the $S_H$ of the native protein. The data points that lie above the dashed line in each plot indicate an $S_H$ higher than the native protein. Such data points indicate a false positive result, and may be eliminated. Thus, most all of the decoy proteins have a lower $S_H$ than the corresponding native protein. Table 3, shown below, shows the number and percentage of decoy proteins that have $S_H$ less than the corresponding native protein.

TABLE 3

| Decoy Set | PDB entry | $S_H$ | Total decoys | % |
|---|---|---|---|---|
| Park & Levitt | 3icb | 651 | 654 | 99.5 |
| | 1ctf | 627 | 631 | 99.4 |
| | 1r69 | 664 | 676 | 98.2 |
| | 2cro | 637 | 675 | 94.4 |
| Baker | 2ezh | 957 | 1000 | 95.7 |
| | 1mzm | 864 | 1000 | 86.4 |
| | 1nkl | 848 | 1000 | 84.8 |
| | 1ctf | 816 | 1000 | 81.6 |
| | 1r69 | 656 | 1000 | 65.6 |
| | 2fow | 627 | 1000 | 62.7 |
| | 2ptl | 619 | 1000 | 61.9 |
| | 1sro | 559 | 1000 | 55.9 |
| | 1c5a | 493 | 991 | 49.8 |
| | 1hsn | 245 | 970 | 25.4 |
| | 1leb | 253 | 1000 | 25.3 |

In Table 3, the percentages shown are of decoy proteins that have an $S_H$ less than the corresponding native protein. As such, 99.5%, 99.4%, 98.2% and 94.4% of the decoy proteins have an $S_H$ below the $S_H$ of the corresponding native protein (3icb, 1ctf, 1r69 and 2cro, respectively). Fewer than 0.5-0.6% of the decoy proteins derived from native proteins 3icb and 1ctf have an $S_H$ that is greater than that of the corresponding native proteins. By comparison, proteins 2cro and 1r69 show a slightly greater number of decoy proteins with a greater $S_H$, and the amino acid residue distribution of the decoy $S_H$ does not exhibit the correlation found for 1ctf and 3icb. Proteins 1r69 and 2cro produce decoy proteins that are uniformly distributed about the RMSD values.

Decoy proteins with a high RMSD typically have a small $S_H$. However, little or no correlation of $S_H$ with RMSD would be visible in native proteins with second-order hydrophobic moment profiles that do not accentuate the hydrophobic core and the hydrophilic regions outside the core. It is then less restrictive for a decoy protein to score well with respect to the native structure.

Figure 7:
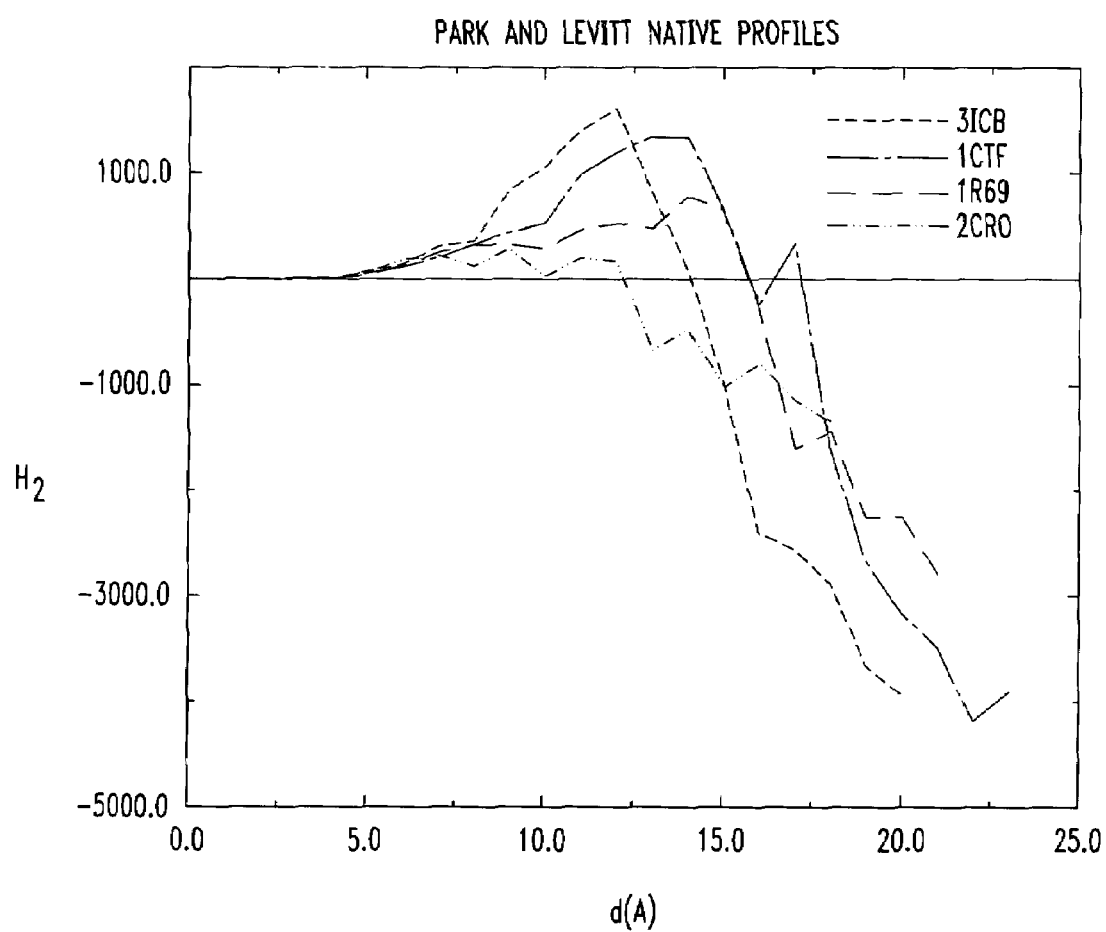
FIG. 7 is a plot showing second-order hydrophobic moments for four native proteins of the Park & Levitt decoy sets.

FIG. 7 is a plot showing the second-order hydrophobic moment profiles of the native proteins from which the four Park & Levitt decoy protein sets are derived, namely 3icb, 1ctf, 1r69 and 2cro. Native proteins 1r69 and 2cro have second-order hydrophobic moment profiles with smaller hydrophobic and hydrophilic regions, and thus a reduced separation of hydrophobic and hydrophilic amino acids residues, than do native proteins 1ctf and 3icb. Thus, it is easier for decoy proteins to have an $S_H$ close to native proteins 1r69 and 2cro, than it is for decoy proteins to have an $S_H$ close to native proteins 1ctf and 3icb. However, few decoy proteins in the Park & Levitt decoy sets have an $S_H$ commensurate with the $S_H$ of 1r69 and 2cro. Typically, if a decoy protein has a large separation of hydrophobic and hydrophilic amino acid residues, it can have an $S_H$ higher than the corresponding native protein, as is exemplified with some of the Baker decoys. As such, using the $S_H$ to rank decoy proteins may provide a more meaningful result when applied to the 1ctf and 3icb decoy sets, which have more prominent native hydrophobic cores and hydrophilic exteriors, as compared to the 1r69 and 2cro decoy sets.

Figure 8:
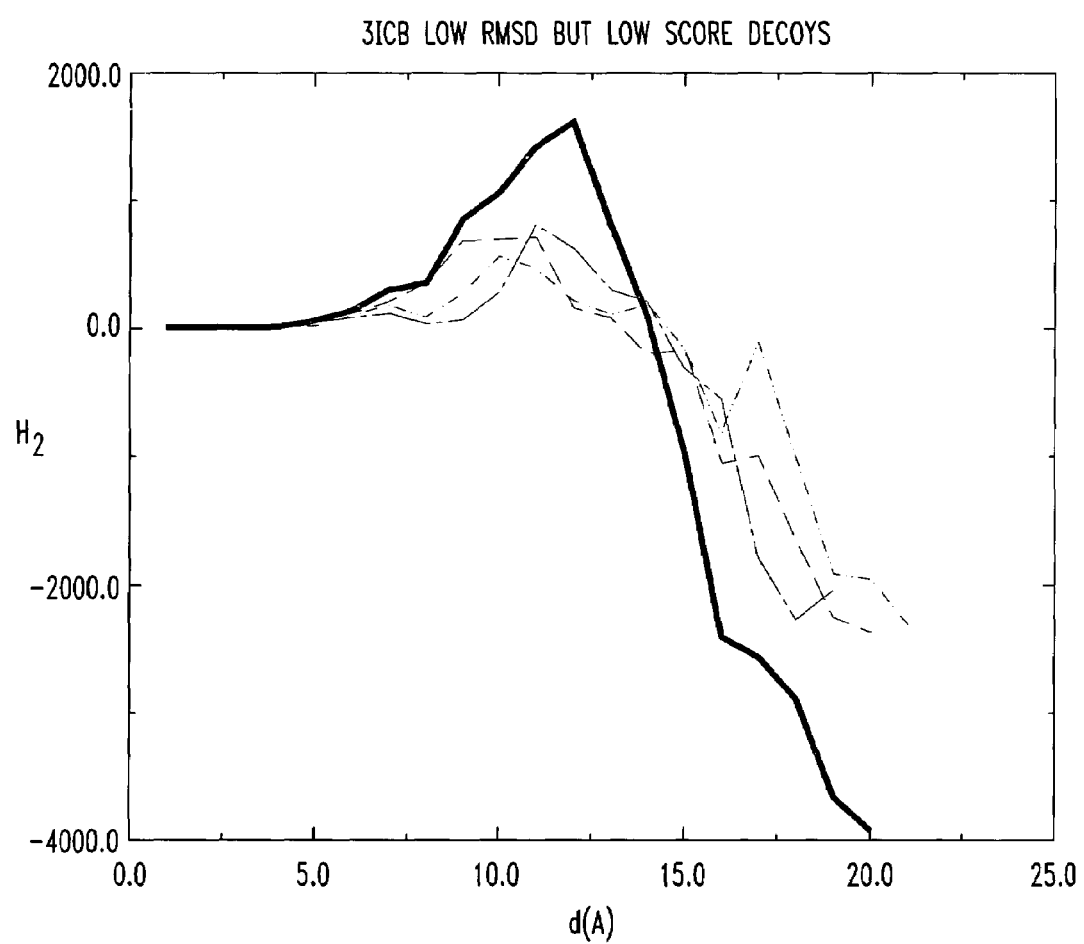
FIG. 8 is a plot showing the second-order hydrophobic moments for decoy proteins of the Park & Levitt decoy set that have a low RMSD but also a low $S_H$ according to an embodiment of the present invention.
Figure 9A:
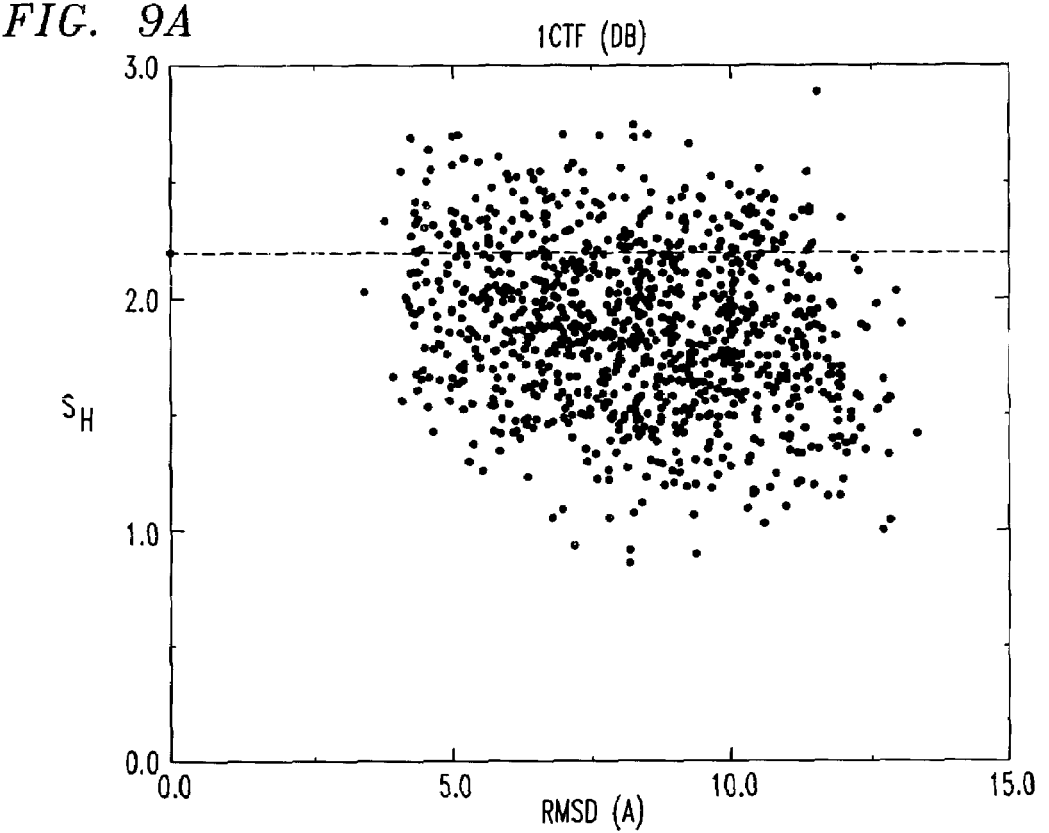
FIGS. 9(A)-(D) are plots showing $S_H$ versus RMSD for Baker decoys according to an embodiment of the present invention.
Figure 9B:
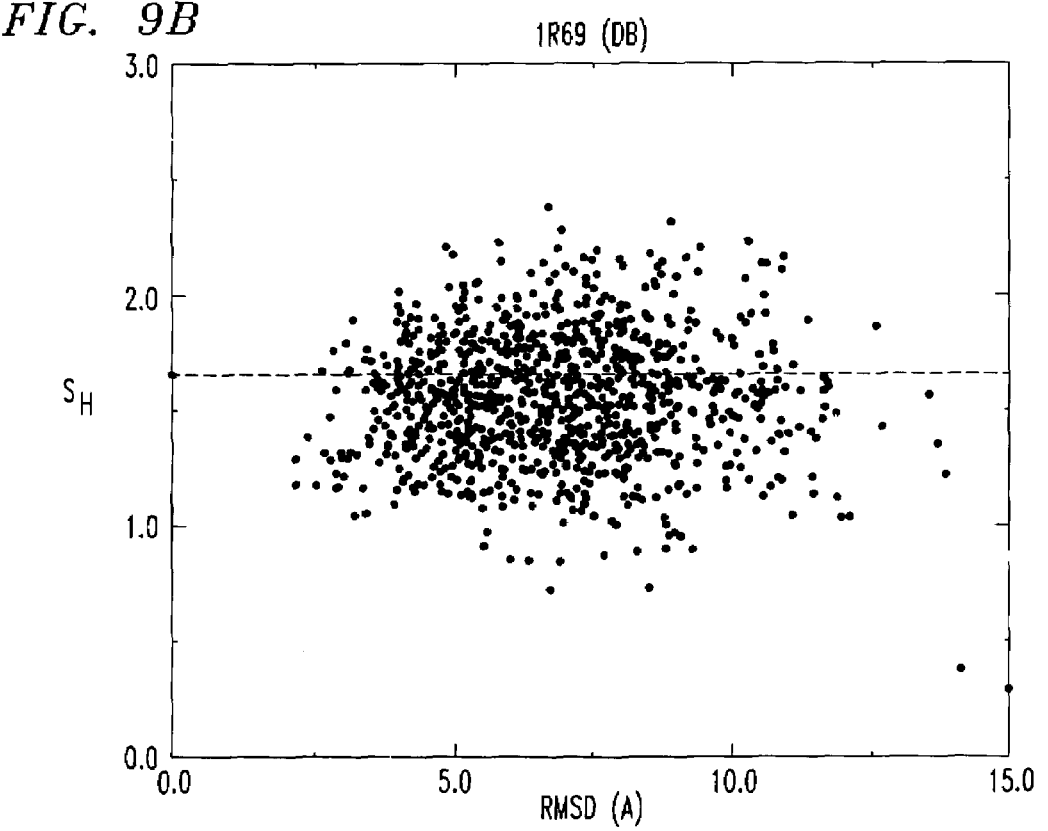
Figure 9C:
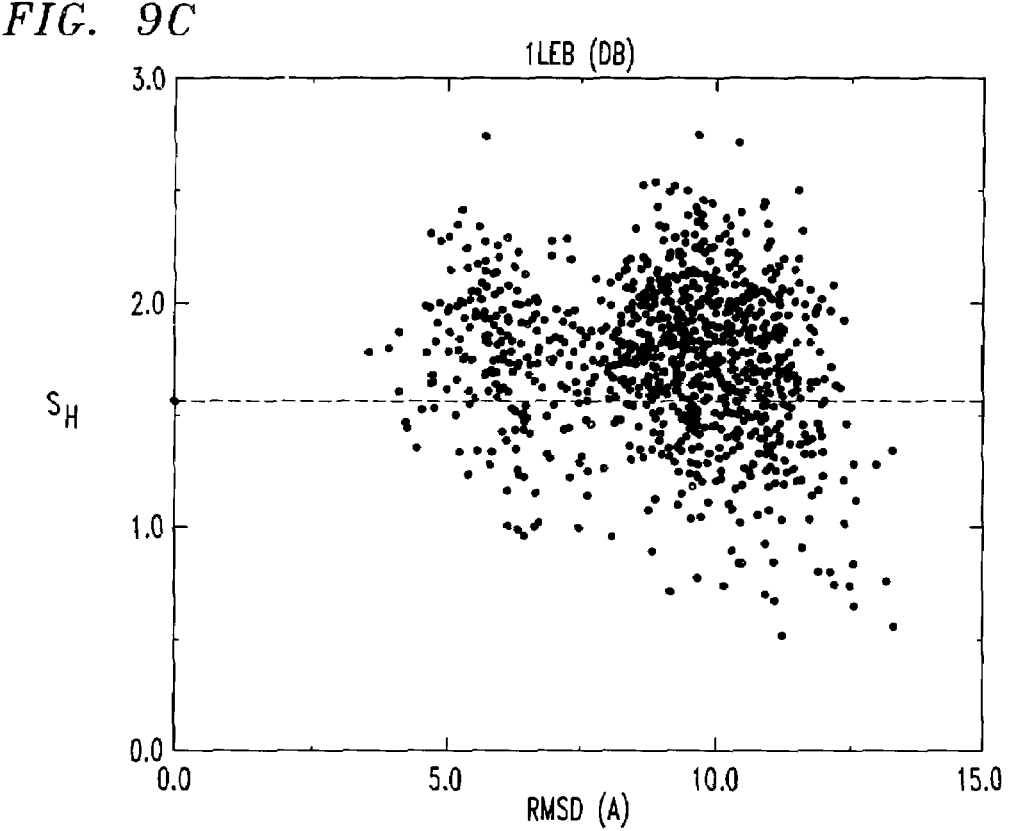
Figure 9D:
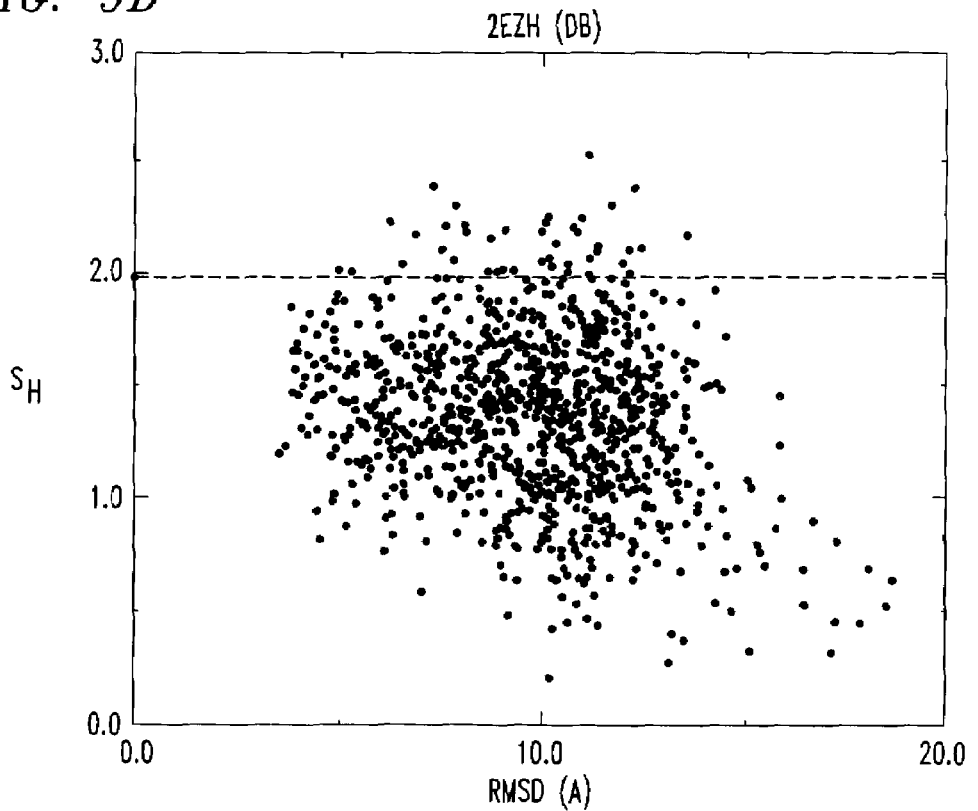

Additionally, there are protein decoys with low RMSD, which is favorable, but also have a low $S_H$, which is unfavorable, even among the decoys of the well correlated sets, such as 3icb. FIG. 8 is a plot showing the second-order hydrophobic moment profiles for the decoy proteins derived from native protein 3icb with an RMSD less than three angstroms, and an $S_H$ less than 1.5, e.g., protein decoys a587, a591 and a8110. The second-order hydrophobic moment profile for native protein 3icb is shown in bold. The $S_H$ for native protein 3icb is 2.89. The decoy proteins shown in FIG. 8 have fewer hydrophobic amino acid residues in their hydrophobic core than is expected for a native protein structure. However, free energy analysis indicates that the decoy proteins shown in FIG. 8 are energetically unfavorable structures according to the reported Optimized Parameters for Liquid Simulation-all-atom (OPLS-AA) force field and the Surface Generalized Born (SGB) model (OPLS-AA/SGB) free energies. The three decoy proteins plotted in FIG. 8, namely, a587, a591 and a8110, have free energy values that are 206.98, 116.94, 110.14 kcal/mol, respectively, greater than native protein 3icb. This indicates that a moderately low overall RMSD, i.e., between about three to five Å, does not necessarily guarantee a high $S_H$, since the overall RMSD is a rather crude descriptor. The overall RMSD does not represent the detailed structural features, i.e., the hydrophobic core. The $S_H$, on the other hand, provides a detailed representation useful in discriminating decoy proteins from native proteins.

FIGS. 9(A)-(D) are plots showing the $S_H$ for four Baker decoy sets, namely, decoys derived from native proteins 1ctf and 1r69 (which are shared with the Park & Levitt decoy set), and decoys derived from native proteins 2ezh and 1leb. The dashed line indicates the $S_H$ of the native protein. The decoys derived from native protein 2ezh have the highest percentage of $S_H$ and the decoys derived from native protein 1leb have the lowest percentage of $S_H$ below the $S_H$ of the corresponding native protein. In contrast to the Park & Levitt decoy sets, the Baker decoy sets show a broader distribution of $S_H$. The percentage of decoy proteins with an $S_H$ below the $S_H$ of the corresponding native protein ranges from 25.3% (1leb) to 95.7% (2ezh), with the majority in the range of 60-80%. Also, most of these decoy protein sets do not exhibit the correlation with RMSD that the decoys derived from native proteins 1ctf and 3icb, in the Park & Levitt decoys, show. Thus, 95.7%, 81.6%, 65.6% and 25.3% of the decoys have an $S_H$ less than native proteins 2ezh, 1ctf, 1r69 and 1leb, respectively.

FIG. 10 is a plot showing the second-order hydrophobic moment profiles of native proteins 2ezh, 1ctf, 1r69 and 1leb of the Baker set. The decoy protein sets with a higher percentage of decoys having an $S_H$ less than the native protein show a more prominent native protein profile than do the decoy protein sets with a lower percentage of decoys having an $S_H$ less than the native protein.

Other decoy proteins in the Baker decoy set show similar behavior. Namely, other decoy protein sets with a higher percentage of decoys with an $S_H$ below the $S_H$ of the native protein, e.g., decoys derived from native proteins 2ezh, 1mzm, 1nkl, 1ctf, show more pronounced native protein profiles than do decoy protein sets with a lower percentage of decoys with an $S_H$ below the $S_H$ of the native protein, e.g., decoys derived from native proteins 1hsn, 1leb. This result may be due in part to the fact that it is easier for decoy proteins to have an $S_H$ approaching or exceeding the $S_H$ of the native protein if the native protein exhibits a reduced separation of hydrophobic and hydrophilic regions.

The reason that there are a relatively large number of Baker decoys with a high $S_H$, as compared to the Park & Levitt decoys, may be due to the manner in which the decoys are generated and selected. For example, it is useful to examine the decoy proteins derived from native proteins 1r69 and 1ctf which are common to both the Park & Levitt decoys, as described above in conjunction with FIG. 4, and to the Baker decoys, as described above in conjunction with FIG. 7.

The Baker decoys have a greater number of decoy proteins with an $S_H$ that is higher than the $S_H$ of the corresponding native protein, as compared to the Park & Levitt decoys. In particular, a significant number of the Baker decoys, derived from native protein 1leb, clearly show a greater spatial segregation of hydrophobic and hydrophilic amino acid residues than is observed for the native protein. The calculation of the radii of gyration (Rg) for the Baker decoys reveals that the Baker decoys have slightly larger Rg values than the Park & Levitt decoys. For example, decoys derived from native protein 1r69 have a Rg of 12.00±0.81 Å in the Baker set and an Rg of 10.99±0.53 Å in the Park & Levitt set. Similarly, decoys derived from native protein 1ctf have an Rg of 11.65±0.66 Å in the Baker set and an Rg of 11.19±0.59 Å in the Park & Levitt set. Perhaps a larger Rg provides a greater spatial freedom to segregate the hydrophobic from the hydrophilic amino acid residues.

Importantly, a point of relevance centers on the way the ab-initio decoys are selected. One of the fundamental assumptions underlying the selection is that the distribution of conformations sampled for a given nine amino acid residue segment of a peptide chain is well approximated by the distributions found in known protein structures contained in the PDB Databank. Fragment libraries for each three and nine amino acid residue segment of the peptide chain are extracted from the PDB Databank using a sequence profile-profile comparison method. The conformational space defined by these fragments is then searched using a Monte Carlo procedure with an energy function that favors compact structures with paired β strands and buried hydrophobic amino acid residues. The favoring of buried hydrophobic amino acid residues in the energy function provides the Baker decoy sets with a greater segregation of hydrophobic and hydrophilic amino acid residues from the hydrophobic protein core to the hydrophilic exterior and consequently provides a higher $S_H$ than is achieved by the Park & Levitt decoy sets.

Decoy proteins derived from small globular soluble native proteins have provided test sets for the evaluation of free energy functions used in the ab-initio prediction of native protein structures. While an ideal objective would be the determination of a free energy function that selects structures that are either minimally displaced spatially from the native structure or a function that selects the native structure itself, success has not been forthcoming. The difficulty in determining an appropriate free energy function is due in part to the manner in which the entropic character of solvation is addressed. One invariant structural feature of soluble globular proteins, that arises from the character of solvation, is the ubiquitous hydrophobic core and hydrophilic exterior. This feature has been used to identify protein structures that do or do not approximate the native protein structure. Considerations of hydrophobicity together with free energy approaches can provide a more selective procedure than the use of either alone.

The free energies of the Park & Levitt decoys have been calculated using the OPLSAA force field and a Surface Generalized Born (SGB) model for a continuum solvent. Without the free energy for a continuum solvent, the OPLSAA gas phase energies are not sufficient to distinguish native-like from non-native-like proteins. Similar results were obtained using the Assisted Model Building with Energy Refinement (AMBER) force field with a Poisson Boltzmann Surface Area (PBSA) continuum solvent model.

Figure 11:
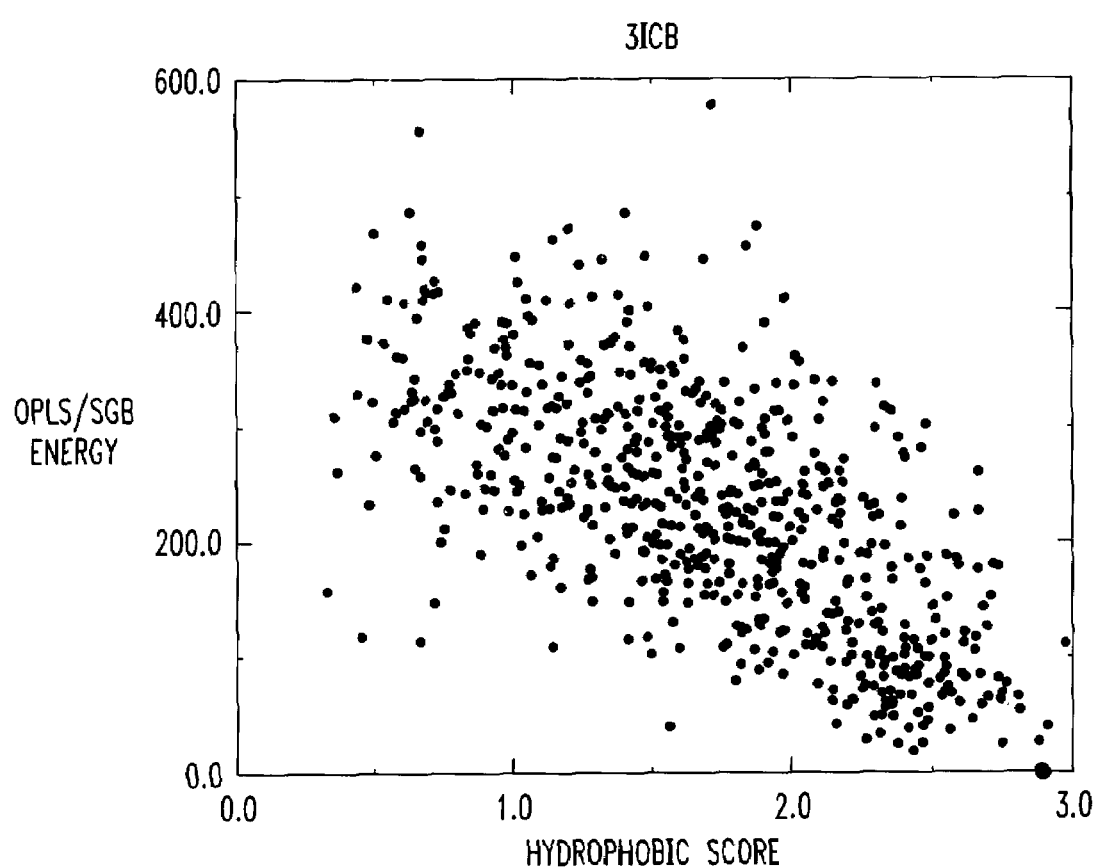
FIG. 11 is a plot showing $S_H$ versus a free energy function based on the Optimized Parameters for Liquid Simulation-all-atom (OPLS-AA) force field and the Surface Generalized Born (SGB) model (OPLS-AA/SGB) for Park & Levitt decoys according to an embodiment of the present invention.

FIG. 11 is a plot showing the OPLSAA/SGB energy (the energy of the native protein is set at zero) versus the $S_H$ for the decoys derived from native protein 3icb of the Park & Levitt set. The energy of the native protein 3icb has been set at zero and is shown marked with a larger circle. In the energy calculations, the decoy protein values are minimized to remove bad contacts in energy space, i.e., due to Lennard-Jones repulsions (otherwise the energies could be huge and meaningless). This minimization might result in slight variations in the structures used in the free energy calculations. However, advantageously, variations in the structures that would affect the free energy results significantly would not affect the $S_H$ significantly.

Free energy calculations, on the other hand, are extremely sensitive to smaller differences in structure. The plot of FIG. 11 shows the correlation between the OPLSAA/SGB energy and the $S_H$, i.e., decoys with a smaller $S_H$ have a higher free energy as compared to the corresponding native protein, and decoys with a greater $S_H$ are closer in free energy to the corresponding native protein. Native protein 1ctf and the decoys derived therefrom, also show a significant correlation between the OPLSAA/SGB energy and the $S_H$, similar to 3icb. However, native proteins 1r69 and 2cro and the decoys derived therefrom, respectively, show a weaker correlation between the OPLSAA/SGB energy and the $S_H$. This weak correlation reflects a weak correlation between the $S_H$ and RMSD as described above.

Interestingly, there are decoy proteins with low OPLSAA/SGB free energies that do not have a high $S_H$. This occurrence is observed even for the decoys derived from native protein 3icb, which show a strong correlation between $S_H$ and RMSD. Decoy sets showing a poorer correlation between $S_H$ and RMSD have a greater number of decoys exhibiting low OPLSAA/SGB free energies and a low $S_H$.

Figure 12:
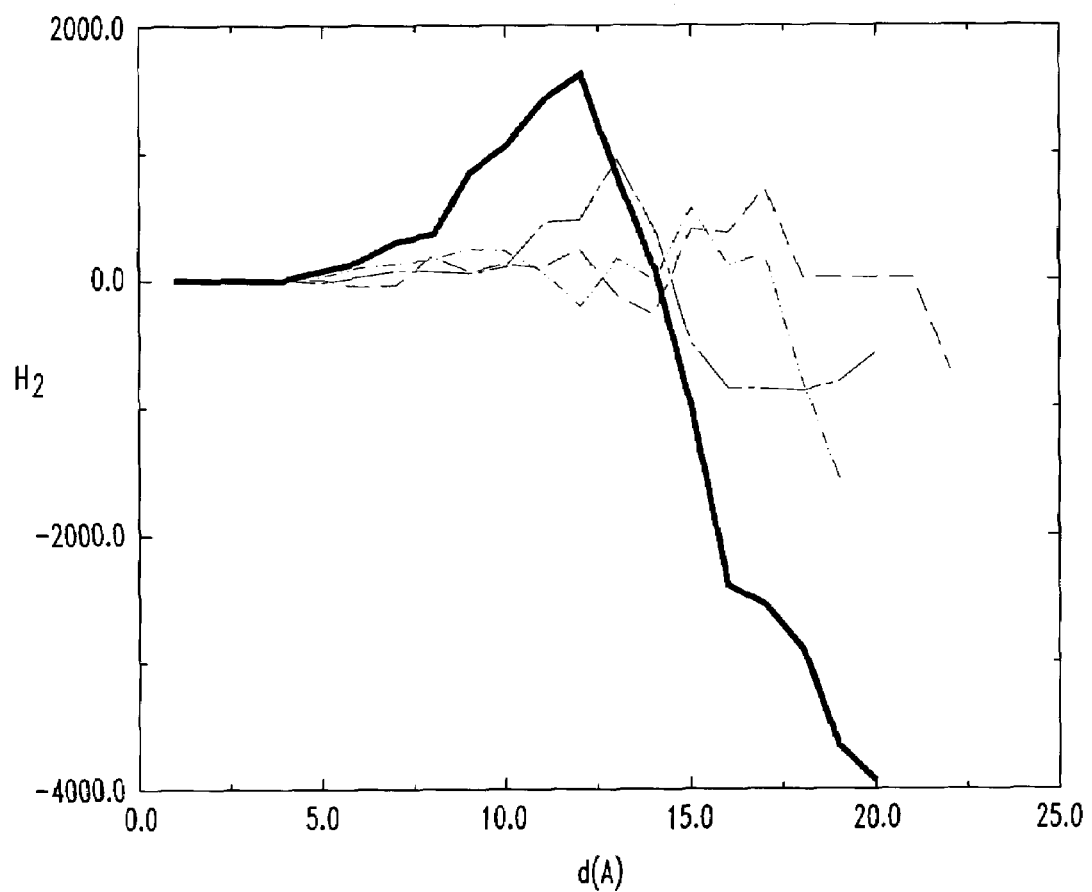
FIG. 12 is a plot showing second-order hydrophobic moments for decoy proteins from the Park & Levitt decoy set with low OPLSAA/SGB energy structures but low $S_H$ according to an embodiment of the present invention.

FIG. 12 is a plot showing several representative second-order hydrophobic moment profiles of decoy proteins derived from native protein 3icb with low free energies and also low $S_H$, i.e., less than 1.0. The $S_H$ for native protein 3icb is 2.89. The decoys shown in FIG. 12 are not the same as those decoys that exhibit a low RMSD and a low $S_H$, as described above in conjunction with FIG. 8. Here, the low $S_H$ indicates that the decoy proteins have a poorly formed hydrophobic core and a poorly formed hydrophilic exterior, even though the free energy value is low. The second-order hydrophobic moment profile of native protein 3icb is shown in bold. By comparison to the data for the native protein, it is evident that the hydrophobic core of the decoys has been "damaged". This alteration of the hydrophobic core is further evidenced by the region of positive moment as seen in the second-order hydrophobic moment profiles of the decoys. The region of positive moment, which may be identified as a hydrophobic core region, is shifted out to a greater distance than is shown for the native protein. Furthermore, none of the decoys exhibit the sharp plunge to negative values outside the hydrophobic core, as is expected for a native protein structure. Thus, a low free energy value does not guarantee a favorable $S_H$. As such, the $S_H$ provides complementary information to that obtained from free energy calculations.

Figure 13A:
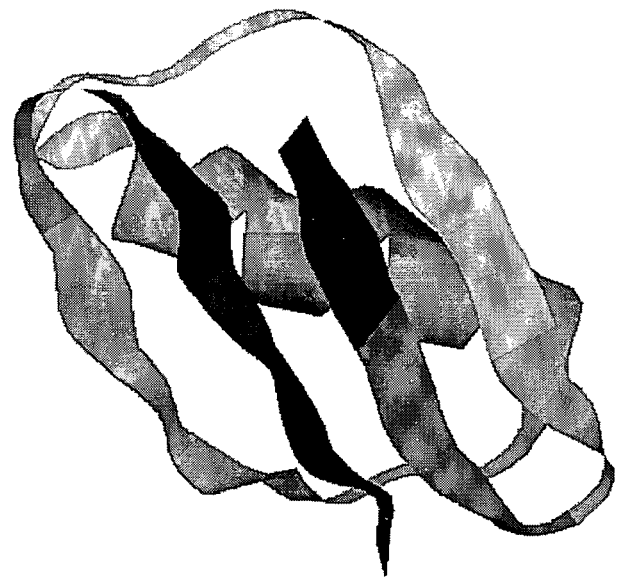
FIGS. 13(A)-(B) are a representation of the structure of Protein G.
Figure 13B:
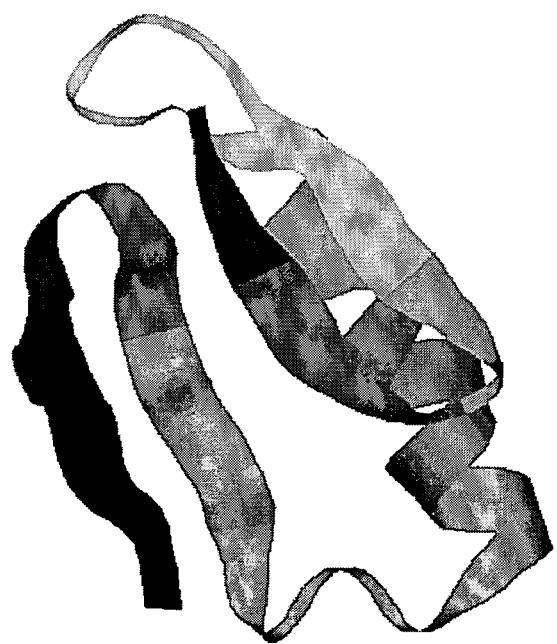

The second-order hydrophobic moment profiling applies to the radial distribution of hydrophobicity but not the angular distribution. FIGS. 13(A)-(B) are a representation of the structure of protein G which show this limitation of the hydrophobic profiling. FIG. 13(A) shows the structure of native protein G, and FIG. 13(B) shows the decoy protein derived from native protein G, i.e., native protein 1gb1 (qa1gb1010-low.pdb) chosen from the Baker decoys. Since native protein 1gb1 has less than 60 amino acid residues, it was not included with the decoy sets previously selected for detailed examination. Native protein 1gb1 does, however, provide an interesting example to exhibit the limitations of the present method. Native protein 1gb1 has a C-terminus and N-terminus forming an anti-parallel β-sheet, while the decoy protein derived from native protein 1gb1 has a β-sheet formed between the C-terminus with another beta strand from residue LYS-9 to THR-16, instead of the N-terminus. This rearrangement of the β-sheets results in a 5.62 Å RMSD from the native protein.

Figure 14:
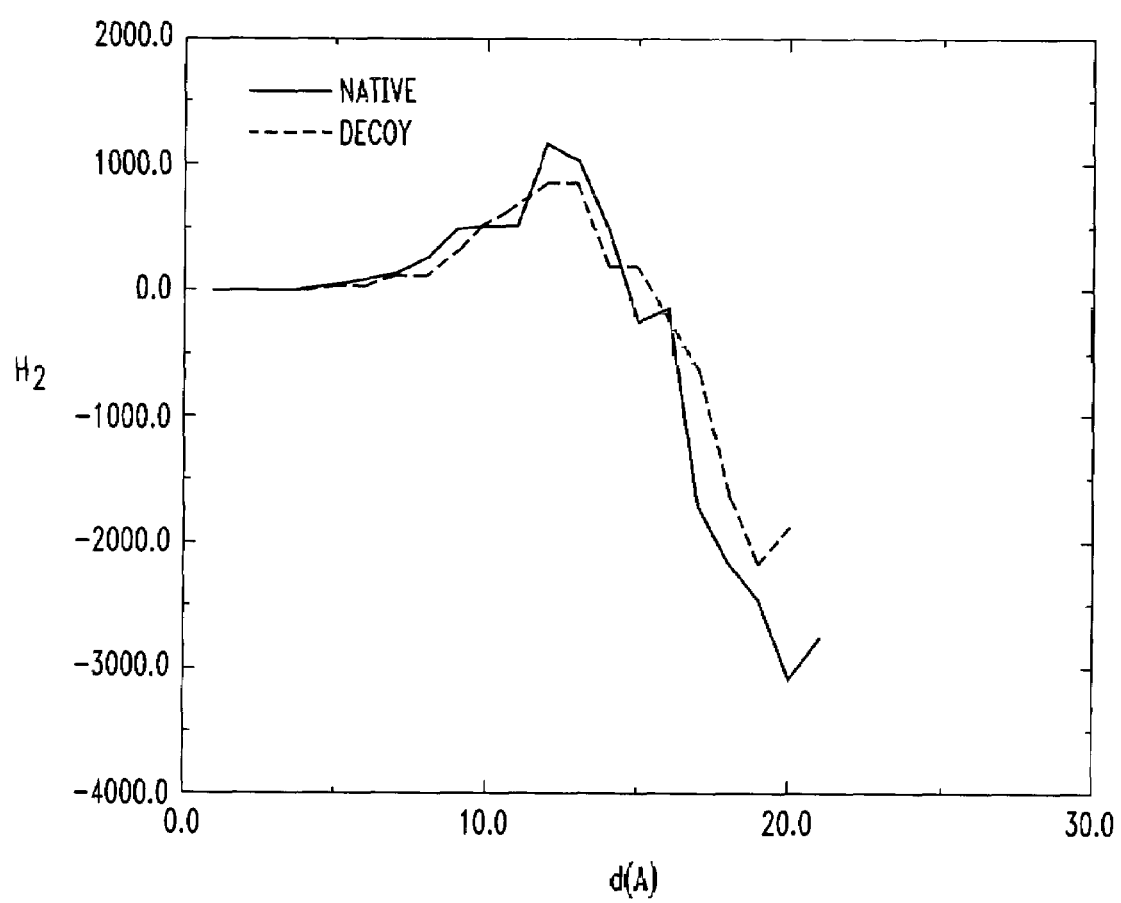
FIG. 14 is a plot showing the second-order hydrophobic moment for Protein G (1gb1).

With respect to the second-order hydrophobic moment profiling, the radial spatial distribution of amino acid residues is hardly affected, since the interchanged amino acid residues are still distributed at roughly the same distance from the centroid, as is shown in FIG. 14. FIG. 14 is a plot showing the second-order hydrophobic moment for protein G. This shows that decoys with large RMSD deviations from the corresponding native protein may show a high $S_H$. On the other hand, complementary information may eliminate decoy candidate proteins, e.g., the OPLSAA/SGB energy of the native protein 1gb1 is −3209.03 kcal/mol, while the energy of the decoy derived from native protein 1gb1 is −3114.06 kcal/mol, i.e., 94.97 kcal/mol higher. Thus, in general, it is easier to create alternate tertiary arrangements while maintaining the ellipsoidal hydrophobicity profile for small proteins as compared to large proteins.

Although illustrative embodiments of the present invention have been described herein, it is to be understood that the invention is not limited to those precise embodiments, and that various other changes and modifications may be made by one skilled in the art without departing from the scope or spirit of the invention.

What is claimed is:

1. A method of analysis of one or more decoy proteins to determine whether a decoy protein has a structure of a native globular protein, comprising:

determining a normalized second-order hydrophobic moment profile for each decoy protein;

using the normalized second-order hydrophobic moment profile to determine a scoring function for analysis of each decoy protein;

using the scoring function to generate a score for each decoy protein, wherein the scoring function comprises $S_H = \int_0^1 |\vec{H}_2| ds$, wherein the score comprises an integral of an area under the normalized second-order hydrophobic moment profile of each protein, and wherein the score measures a prominence of a hydrophobic core and a prominence of a hydrophilic exterior of each decoy protein;

outputting the score for each decoy protein to at least one of a user, a display, a memory and one or more additional computers on a network; and using the score of each decoy protein to determine whether the decoy protein has a structure of a native globular protein.

2. The method of claim 1, wherein at least one of the one or more decoy proteins is a native protein.

3. The method of claim 1, further comprising the step of comparing the scores generated for the one or more decoy proteins.

4. The method of claim 3, wherein the step of comparing comprises ranking the structures.

5. The method of claim 1, wherein each decoy protein is a native-like decoy protein structure.

6. The method of claim 1, wherein each decoy protein comprises greater than or equal to about 60 amino acid residues.

7. The method of claim 1, wherein the one or more decoy proteins comprises a plurality of decoy proteins organized into subsets.

* * * * *